US008263092B1

(12) United States Patent
Smith et al.

(10) Patent No.: US 8,263,092 B1
(45) Date of Patent: Sep. 11, 2012

(54) ALPHAVIRUS REPLICON PARTICLES AS IMMUNOLOGICAL ADJUVANTS

(75) Inventors: Jonathan F. Smith, Cary, NC (US); Bolyn Hubby, Cary, NC (US); Peter Berglund, Chapel Hill, NC (US); Laura Copp, Raleigh, NC (US); Whitney Ellis, Oxford, NC (US)

(73) Assignee: AlphaVax, Inc., Research Triangle Park, NC (US)

( * ) Notice: Subject to any disclaimer, the term of this patent is extended or adjusted under 35 U.S.C. 154(b) by 1247 days.

(21) Appl. No.: 11/854,472

(22) Filed: Sep. 12, 2007

Related U.S. Application Data

(60) Provisional application No. 60/825,394, filed on Sep. 12, 2006.

(51) Int. Cl.
*A61K 45/00* (2006.01)
*A61K 39/295* (2006.01)
*A61K 39/193* (2006.01)

(52) U.S. Cl. ................. 424/281.1; 424/199.1; 424/93.2; 424/85.2

(58) Field of Classification Search ........................ None
See application file for complete search history.

(56) References Cited

U.S. PATENT DOCUMENTS

| | | | |
|---|---|---|---|
| 4,650,764 | A | 3/1987 | Temin et al. |
| 5,185,440 | A | 2/1993 | Davis et al. |
| 5,505,947 | A | 4/1996 | Johnston et al. |
| 5,643,576 | A | 7/1997 | Johnston et al. |
| 5,789,245 | A | 8/1998 | Dubensky, Jr. et al. |
| 5,792,462 | A | 8/1998 | Johnston et al. |
| 5,814,482 | A | 9/1998 | Dubensky, Jr. et al. |
| 5,843,723 | A | 12/1998 | Dubensky, Jr. et al. |
| 6,015,686 | A | 1/2000 | Dubensky, Jr. et al. |
| 6,015,694 | A | 1/2000 | Dubensky, Jr. et al. |
| 6,156,558 | A | 12/2000 | Johnston et al. |
| 6,190,666 | B1 | 2/2001 | Garoff et al. |
| 6,242,259 | B1 | 6/2001 | Polo et al. |
| 6,376,236 | B1 | 4/2002 | Dubensky, Jr. et al. |
| 7,045,335 | B2 | 5/2006 | Smith et al. |
| 7,078,218 | B2 | 7/2006 | Smith et al. |
| 2001/0016199 | A1 | 8/2001 | Johnston et al. |
| 2002/0015945 | A1 | 2/2002 | Polo et al. |
| 2002/0086837 | A1 | 7/2002 | Gauldie et al. |
| 2002/0165172 | A1 | 11/2002 | Sallberg et al. |
| 2004/0208848 | A1 | 10/2004 | Smith et al. |
| 2005/0031592 | A1 | 2/2005 | Doolan et al. |
| 2005/0266550 | A1 | 12/2005 | Rayner et al. |

FOREIGN PATENT DOCUMENTS

| | | | |
|---|---|---|---|
| WO | WO 92/10578 | | 6/1992 |
| WO | WO 01/12172 | | 2/2001 |
| WO | WO 2004/085660 | | 10/2004 |
| WO | WO 2006/085983 | * | 8/2006 |

OTHER PUBLICATIONS

Rodriguez-Madoz et al (Molecular Therapy 12:153-163, 2005).*
Abaitua et al (Virus Research 116:11-20, 2006).*
Colmenero et al (International Journal of Cancer 98:554-560, 2002).*
Abaitua et al. (Mar. 1, 2006) "Improving Recombinant MVA Immune Responses: Potentiation of the Immune Responses to HIV-1 with MVA and DNA Vectors Expressing Env and the Cytokines IL-12 and IFN0gamma," *Virus Res.* 116(1-2):11-20.
Bernard et al. (2000) "Mutations in the E2 Glycoprotein of Venezuelan Equine Encephalitis Virus Confer Heparan Sulfate Interaction, Low Morbidity, and Rapid Clearance from Blood of Mice," *Virology* 276:93-103.
Chen et al. (Jun. 15, 2001) "Suppression of Immune Response and Protective Immunity to a Japanese Encephalitis Virus DNA Vaccine by Coadministration of an Il-12-Expressing Plasmid," *J. Immunol.* 166(12):7419-7426.
Colmenero et al. (2002) "Immunotherapy with Recombinant SFV-Replicons Expressing the P815A Tumor Antigen or IL-12 Induces Tumor Regression," *Int. J. Cancer* 98:554-5603.
Cooper et al. (Online Jun. 15, 2004) "Interleukin-12 Redirects Murine Immune Responses to Soluble or Aluminum Phosphate Adsorbed HSV-2 Glycoprotein D Towards Th1 and CD4+ CTL Responses," *Vaccine* 23:236-246.
Davis et al. (1990) *Microbiology* 4$^{th}$ ed. pp. 156-158.
Frolov et al. (Oct. 1996) "Alphavirus-Based Expression Vectors: Strategies and Applications," *Proc. Nat. Acad. Sci. USA* 93:11371-11377.
Gherardi et al. (Jul. 2000) "Interleukin-12 (IL-12—Enhancement of the Cellular Immune Response Against Human Immunodeficiency Virus Type 1 Env Antigen in a DNA Prime/Vaccinia Virus Boost Vaccine Regimen is Time and Dose Dependent: Suppressive Effects of IL-12 Boost are Mediated by Nitric Oxide," *J. Virol.* 74(14):6278-6286.
Glasgow et al. (Dec. 1991) "Two Mutations in the Envelope Glycoprotein E2 of Semliki Forest Virus Affecting the Maturation and Entry Patterns of the Virus Alter Pathogenicity for Mice," *Virology* 185(2):741-748.
Hahn et al. (Apr. 1992) "Infectious Sindbis Virus Transient Expression Vectors for Studying Antigen Processing and Presentation," *Proc. Nat. Acad. Sci. USA* 89:2679-2683.
Heidner et al. (Dec. 1994) "The Amino-Terminal Residue of Sindbis Virus Glycoprotein E2 Influences Virus Maturation, Specific Infectivity for BHK Cells, and Virulence in Mice," *J. Virol.* 68(12):8064-8070.
Heise et al. (May 2000) "A Single Amino Acid Change in nsP1 Attenuated Neurovirulence of the Sindbis-Group Alphavirus S.A. AR86," *J. Virol.* 74(9):4207-4213.
International Search Report, Corresponding to International Application No. PCT/US2007/078314, Mailed Sep. 25, 2008.
Kinney et al. (1989) "The Full-Length Nucleotide Sequences of the Virulent Trinidad Donkey Strain of Venezuelan Equine Encephalitis Virus and Its Attenuated Vaccine Derivative, Strain TC-83," *Virology* 170:19-30.
Klimstra et al. (Dec. 1999) "Infection of Neonatal Mice with Sindbis Virus Results in a Systemic Inflammatory Response Syndrome," *J. Virol.* 73(12):10387-10398.

(Continued)

*Primary Examiner* — Mary E Mosher
(74) *Attorney, Agent, or Firm* — Greenlee Sullivan P.C.

(57) ABSTRACT

The immune response to an antigen of interest, either in purified form or expressed via an alphavirus replicon particle, can be enhanced by the simultaneous administration of an alphavirus replicon particle which expresses interleukin-12. This allows for the use of significantly smaller quantities of the antigen and this immunization strategy can also eliminate the need for boosting administration of the antigen or it can reduce the number of boosts required for an effective immune response to the antigen.

17 Claims, 19 Drawing Sheets

OTHER PUBLICATIONS

Polo et al. (Sep. 1990) "Attenuating Mutations in Glycoproteins E1

Kunkel, T.A. (Jan. 1985) "Rapid and Efficient Site-Specific Mutagenesis without Phenotypic Selection," *Proc. Nat. Acad. Sci. USA* 82:488-492.

Lu et al. (2001) "Transmission of Replication-Defective Sindbis Helper Vectors Encoding Capsid and Envelope Proteins," *J. Virol. Methods* 91(1):59-65.

Olmsted et al. (Jul. 27, 1984) "Sindbis Virus Mutants Selected for Rapid Growth in Cell Culture Display Attenuated Virulence in Animals," *Science* 225:424-427.

Pedersen et al. (Oct. 1974) "Separation, Isolation, and Immunological Studies of the Structural Proteins of Venezuelan Equine Encephalomyelitis Virus," *J. Virol.* 14(4):740-744. and E2 of Sindbis Virus Produce a Highly Attenuated Strain When Combined In Vitro," *J. Virol.* 64(9):4438-4444.

Pushko et al. (1997) "Replicon-Helper Systems from Attenuated Venezuelan Equine Encephalitis Virus: Expression of Hererologous Geens in Vitro and Immunization Against Heterologous Pathogens in Vivo," *Virology* 239:389-401.

Rayner et al. (Sep. 1, 2002) "Alphavirus Vectors and Vaccination," *Rev. Med. Virol.* 12(5):279-296.

Rodriguez-Madoz et al. (Online Apr. 12, 2005) "Semliki Forest Virus Vectors Engineered to Express Higher IL-12 Levels Induce Efficient Elimination of Murine Colon Adenocarcinomas," *Mol. Ther.* 12(1):153-163.

Rosenberg, S.A. (Mar. 1999) "A New Era for Cancer Immunotherapy Based on the Genes that Encode Cancer Antigens," *Immunity* 10:281-287.

Schadeck et al. (Online Oct. 26, 2005) "A Dose Sparing Effect by Plasmid Encoded IL-12 Adjuvant on a SIVgag-Plasmid DNA Vaccine in Rhesus Macaques," *Vaccine* 24:4677-4687.

Schlesinger et al. (1986) "Defective RNAs of Alphaviruses," In; *The Togaviridae and Flaviviridae*, Plenum Publishing Corp., New York, Ch. 6, 149-169.

Smerdou et al. (Feb. 1999) "Two-Helper RNA System for Production of Recombinant Semliki Forest Virus Particles," *J. Virol.* 73(2):1092-1098.

Smit et al. (Nov. 2001) "PE2 Cleavage Mutants of Sindbis Virus: Correlation Between Viral Infectivity and pH-Dependent Membrane Fusion Activation of the Spike Heterodimer," *J. Virol.* 75(22):11196-11204.

Thompson et al. (Mar. 7, 2006) "Mucosal and Systemic Adjuvant Activity of Alphavirus Replicon Particles," *Proc. Nat. Acad. Sci. USA* 103(10):3722-3727.

White et al. (Apr. 2001) "Role of Alpha/Beta Interferon in Venezuelan Equine Encephalitis Virus Pathogenesis: Effect of an Attenuating Mutation in the 5' Untranslated Region," *J. Virol.* 75:3706-3718.

Written Opinion, Corresponding to International Application No. PCT/US2007/078314, Mailed Sep. 25, 2008.

EP First Office Action, dated Mar. 12, 2010, in European Patent Application No. 07872297.2, corresponding to present application, 4 pp.

Response to First EP Office Action, dated Sep. 14, 2010, in European Patent Application No. 07872297.2, corresponding to present application, 7 pp.

New Zealand First Office Action, dated Jul. 14, 2010, in New Zealand Patent Application No. 575476, corresponding to present application, 2 pp.

Response to First New Zealand Office Action, dated Sep. 29, 2011, in New Zealand Patent Application No. 575476, corresponding to present application, 2 pp.

New Zealand Supplemental Amendment to First Office Action, dated Oct. 13, 2011, in New Zealand Patent Application No. 575476, corresponding to present application, 2 pp.

New Zealand Second Office Action, dated Oct. 18, 2011, in New Zealand Patent Application No. 575476, corresponding to present application, 2 pp.

Response to Second New Zealand Office Action, dated Mar. 7, 2012, in New Zealand Patent Application No. 575476, corresponding to present application, 4 pp.

Australian First Office Action, dated Mar. 16, 2012, in Australian Patent Application No. 2007342333 (filed Sep. 7, 2007), corresponding to present application, 2 pp.

\* cited by examiner

ALPHAVIRUS REPLICON PARTICLES AS IMMUNOLOGICAL ADJUVANTS

CROSS-REFERENCE TO RELATED APPLICATIONS

This application claims benefit of U.S. Provisional Application 60/825,394, filed Sep. 12, 2006, which application is incorporated by reference herein to the extent there is no inconsistency with the present disclosure.

STATEMENT REGARDING FEDERALLY SPONSORED RESEARCH OR DEVELOPMENT

Not Applicable

BACKGROUND OF THE INVENTION

The present invention relates to recombinant DNA technology, and in particular to introducing foreign nucleic acid(s) in a eukaryotic cell, and more particularly to methods for producing immunogenic compositions comprising infective virus particles or virus-like particles in high yields, especially particles expressing interleukin-12 useful in immunotherapies, vaccines and/or gene therapy applications. In particular, the present disclosure provides alphavirus replicon particle (ARP) preparations, especially those expressing interleukin 12 (IL-12), suitable for use in human and veterinary medicine and for enhancing the immune system's response to a concurrently administered antigen.

The Alphavirus genus includes a variety of viruses, all of which are members of the Togaviridae family. The alphaviruses include Eastern Equine Encephalitis Virus (EEE), Venezuelan Equine Encephalitis Virus (VEE), Everglades Virus, Mucambo Virus, Pixuna Virus, Western Equine Encephalitis Virus (WEE), Sindbis Virus, Semliki Forest Virus, Middleburg Virus, Chikungunya Virus, O'nyong-nyong Virus, Ross River Virus, Barmah Forest Virus, Getah Virus, Sagiyama Virus, Bebaru Virus, Mayaro Virus, Una Virus, Aura Virus, Whataroa Virus, Babanki Virus, Kyzylagach Virus, Highlands J virus, Fort Morgan Virus, Ndumu Virus, and Buggy Creek Virus. The viral genome is a single-stranded, messenger-sense RNA, modified at the 5'-end with a methylated cap and at the 3'-end with a variable-length poly (A) tract. Structural subunits containing a single viral protein, capsid, associate with the RNA genome in an icosahedral nucleocapsid. In the virion, the capsid is surrounded by a lipid envelope covered with a regular array of transmembrane protein spikes, each of which consists of a heterodimeric complex of two glycoproteins, E1 and E2. See Pedersen et al., *J. Virol* 14:740 (1974). The Sindbis and Semliki Forest viruses are considered the prototypical alphaviruses and have been studied extensively. See Schlesinger, The Togaviridae and Flaviviridae, Plenum Publishing Corp., New York (1986). The VEE virus has been studied extensively, see, e.g., U.S. Pat. No. 5,185,440.

The studies of these viruses have led to the development of techniques for vaccinating against the alphavirus diseases and against other diseases through the use of alphavirus vectors for the introduction of foreign genes. See U.S. Pat. No. 5,185,440 to Davis et al., and PCT Publication WO 92/10578. The use of alphavirus vectors to direct the expression of foreign genes in eukaryotes has become a topic of increasing interest. It is well known that live, attenuated viral vaccines are among the most successful means of controlling viral disease. However, for some virus pathogens, immunization with a live virus strain may be either impractical or unsafe. One alternative strategy is the insertion of sequences encoding immunizing antigens of such agents into a live, replicating strain of another virus. One such system utilizing a live VEE vector is described in U.S. Pat. Nos. 5,505,947 and 5,643,576 to Johnston et al. Another such system is described by Hahn et al., *Proc. Natl. Acad. Sci. USA* 89:2679-2683 (1992), wherein Sindbis virus constructs express a truncated form of the influenza hemagglutinin protein. Another system is the alphavirus replicon system, as described in U.S. Pat. No. 6,190,666 to Garoff et al., U.S. Pat. Nos. 5,792,462 and 6,156,558 to Johnston et al., U.S. Pat. Nos. 5,814,482, 5,843,723, 5,789,245, 6,015,694, 6,105,686 and 6,376,236 to Dubensky et al; U.S. Published Application No. 2002-0015945 A1 (Polo et al.), U.S. Published Application No. 2001-0016199 (Johnston et al.), Frolov et al. (1996) *Proc. Natl. Acad. Sci. USA* 93:11371-11377 and Pushko et al. (1997) *Virology* 239: 389-401. Improved constructs, both helper(s) and replicon, for use in producing alphavirus replicon particles are described in U.S. Pat. No. 7,045,335 (Smith et al.) and WO 2004/085660 (Smith et al.), and novel processes for their manufacture are described in U.S. Pat. No. 7,078,218 (Smith et al.).

There remains a need in the art for methods which allow the production of a more effective immune response to an administered immunogenic composition, especially immunogenic compositions comprising protein antigens, including those expressed from alphavirus replicon particles, especially one comprising less antigen than in a conventional vaccine composition, especially where a protective immune response is sought, such that there is less severe disease, reduced risk of disease or no disease in response to the relevant pathogen.

BRIEF SUMMARY OF THE INVENTION

The present disclosure provides a method of enhancing an immune response to an immunogen in a subject via the co-administration of alphavirus replicon particles expressing IL-12, for example, wherein the immunogen and the alphavirus replicon particles expressing IL-12 are advantageously administered to the subject at the same time and in the same location as the immunogen of interest.

Also provided herein are methods of preventing, reducing the likelihood of contracting or reducing the severity of an infectious disease in a subject comprising administering an immunogen consisting of or derived from the causative micro-organism or virus (or a killed or attenuated derivative thereof) for that infectious disease, and alphavirus replicon particles expressing interleukin-12 (IL-12). The immunogen (used interchangeably with antigen herein) can be a protein, glycoprotein, lipoprotein, the expression product of a minigene which product comprises a linear string of epitopes of interest (for example, from an influenza or other virus hemagglutinin), a toxin, attenuated toxin, inactivated toxin, virus, attenuated virus, inactivated virus, bacterial cells or portion(s) thereof, inactivated bacteria, attenuated bacteria, fungal cells or portion(s) thereof, attenuated fungus, inactivated fungus, parasite or portion(s) thereof, inactivated parasite, attenuated parasite, protozoan or portion(s) thereof, inactivated protozoan or portions thereof, attenuated protozoan, DNA or RNA capable of expressing an antigen or fragments or epitopes thereof, pox virus vectored immunogen, alphavirus-vectored or an adenovirus-vectored immunogen, as well as polysaccharide, lipopolysaccharide, lipooligosaccharide or other material capable of eliciting an immune response in a human or animal to which it is administered.

Further provided is an immunogenic composition, especially a vaccine composition, comprising an immunogen preparation selected from the group consisting of protein or other antigenic material, together with an alphavirus replicon particle which expresses interleukin-12. The immunogen (used interchangeably with antigen herein) can be a protein, glycoprotein, lipoprotein, toxin, attenuated toxin, inactivated toxin, virus, attenuated virus, inactivated virus, bacterial cells or portion(s) thereof, inactivated bacteria, attenuated bacteria, fungal cells or portion(s) thereof, attenuated fungus, inactivated fungus, parasite or portion(s) thereof, inactivated parasite, attenuated parasite, protozoan or portion(s) thereof, inactivated protozoan or portions thereof, attenuated protozoan, DNA capable of expressing an antigen or fragments or epitopes thereof, pox virus vectored immunogen, alphavirus-vectored or an adenovirus-vectored immunogen, tumor cell antigen or tissue or portion thereof, as well as polysaccharide, lipopolysaccharide, lipooligosaccharide or other material capable of eliciting an immune response in a human or animal to which it is administered.

In the compositions and methods described herein, the alphavirus from which the alphavirus replicon particles are derived can be Venezuelan Equine Encephalitis (VEE) virus, desirably an attenuated VEE virus. VEE virus or other alphavirus-derived alphavirus replicon particles can be engineered for the production of IL-12 and/or an immunogen of interest. Where there are ARPs expressing IL-12 administered in conjunction with an immunogen-expressing ARP preparation, the dose of the immunogen-expressing VRP is most preferably equal to or greater than the dose of VEE replicon particles expressing IL-12.

BRIEF DESCRIPTION OF THE DRAWINGS

FIG. 9(A): A single ORF encoding a fusion protein construct of the two IL-12 subunits, p35 and p40, was cloned into the alphavaccine vector downstream of the 26S promoter. FIG. 9 (B): Lysates containing 2 μg of total protein from Vero cells infected with IL-12 VRP and incubated for 16 hours were processed for SDS-PAGE and Western blot using IL-12-specific antiserum. Lanes 2-6 represent recombinant IL-12 at amounts ranging from 40-400 ng, as indicated. The migration of 51 or 28 kDa molecular size markers are indicated in the figure.

VRP; (f) 5×10⁷ CEA VRP+5×10⁷ IL-12 VRP. Humoral responses to CEA were measured with ELISA (solid bars) whereas responses to VRP were determined as neutralizing titers (open bars).

Figure 11:
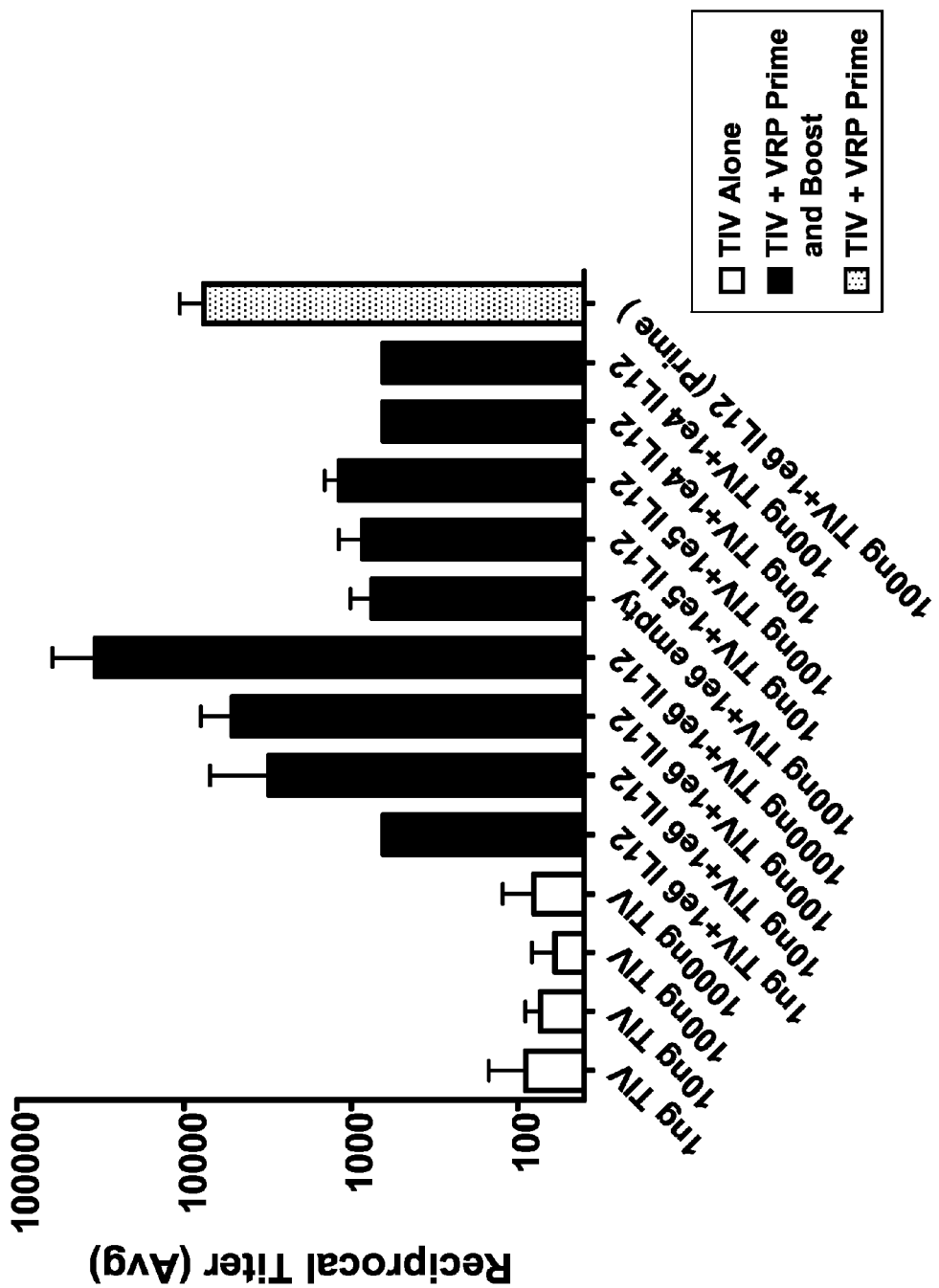

FIG. 11 shows that IL-12 VRP co-administered with TIV significantly enhance humoral immune responses to the influenza A/New Caledonia HA (H1) component of the TIV. Groups of six Balb/c mice were immunized twice, with TIV in doses ranging in 10-fold increments from 1 ng to 1000 ng which was administered alone (white bars) or co-administered (black bars) with IL-12 VRP at doses ranging from 1×10⁴ to 1×10⁶ IU, as indicated. One group received 100 ng of TIV combined with 1×10⁶ IU of empty VRP, as indicated. At one week post-boost, sera were obtained from the animals and analyzed for antibody ELISA titers specific for New Caledonia HA. The rightmost bar represent humoral responses in mice primed with 100 ng of TIV combined with 1×10⁶ IU of IL-12 VRP but boosted with 100 ng of TIV alone.

Figure 12:
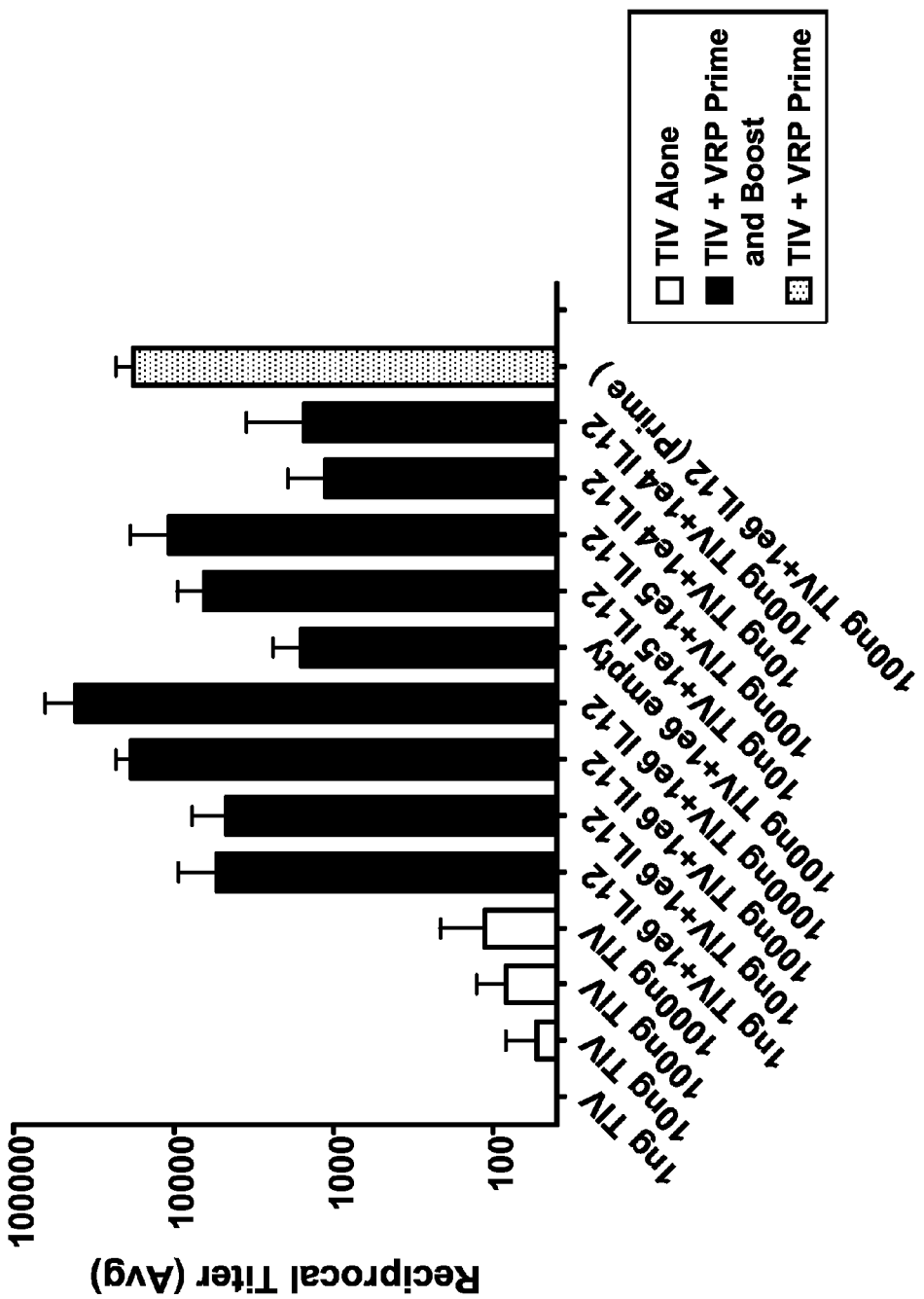

FIG. 12 shows humoral responses to the A/Wyoming (H3) HA component of the TIV in the serum samples collected from the mice as described in FIG. 11.

Figure 13:
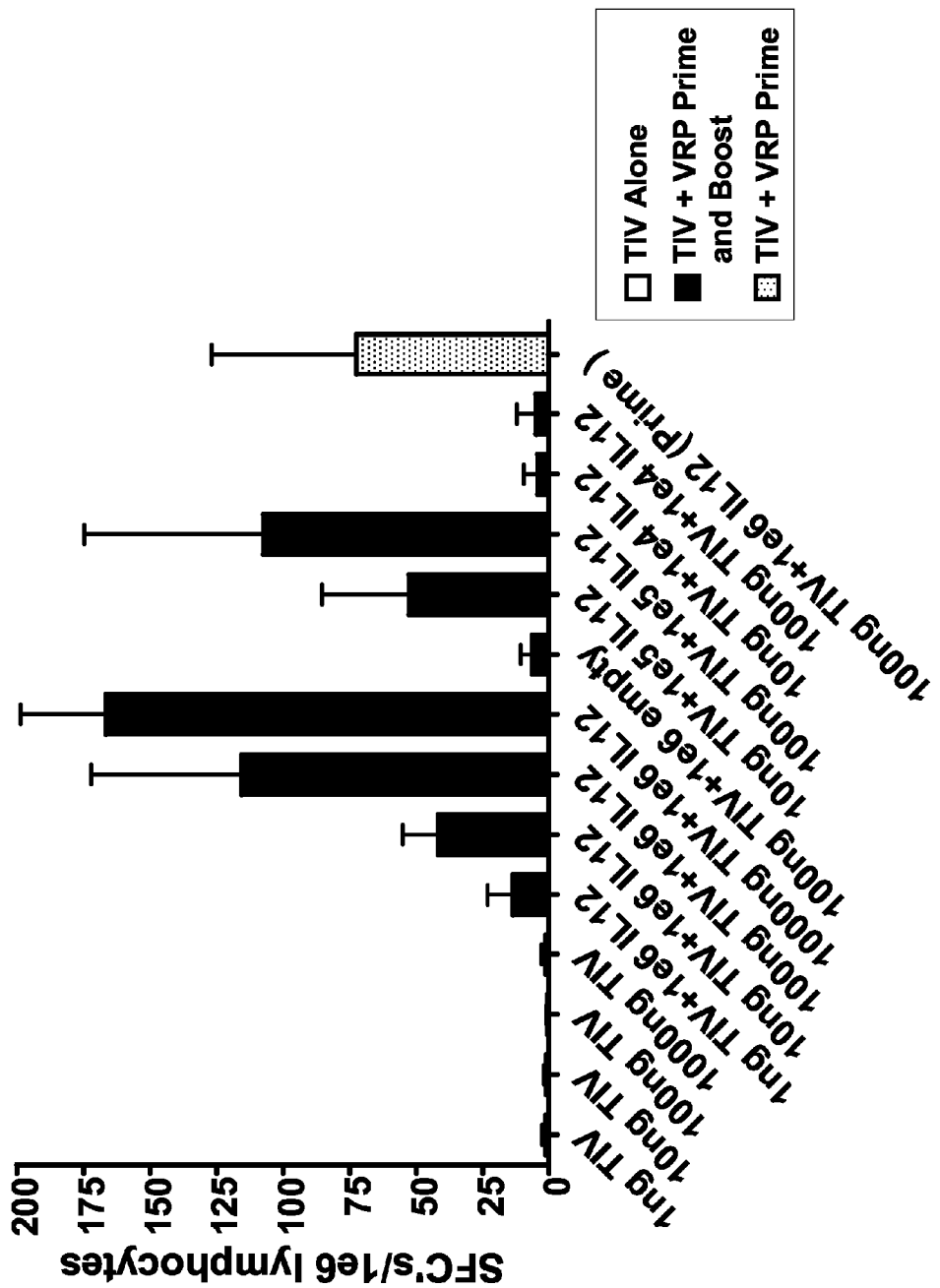

FIG. 13 shows T cell responses to A/Wyoming H3 HA measured by ELISPOT at 7 days post-immunization in mice immunized once with the same inocula as described in FIGS. 11 and 12, above.

Figure 14:
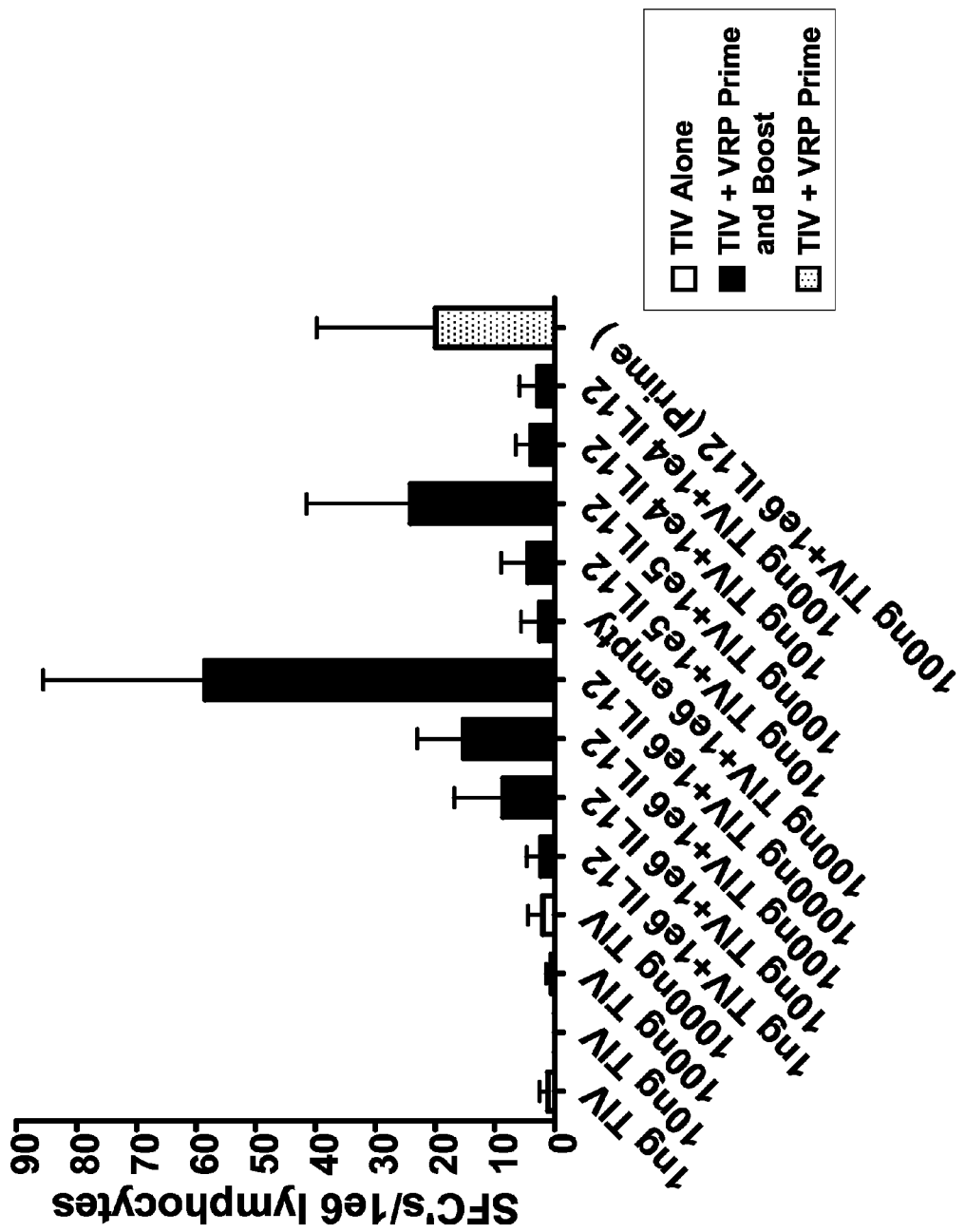

FIG. 14 shows T cell responses to A/Wyoming NA (neuraminidase) measured by ELISPOT at 7 days post-immunization in mice immunized once with the same inocula as described in FIGS. 11 and 12, above.

DETAILED DESCRIPTION OF THE INVENTION

There is a need in the art for cost-effective, potent and dose-sparing vaccine adjuvants, especially with respect to cancer, toxin and influenza vaccines, as well as vaccines for other diseases. Provided herein is an RNA replicon vector system, derived from an attenuated alphavirus, to produce single-cycle, propagation-defective virus-like alphavirus replicon particle (ARP) adjuvants containing a self-replicating RNA (replicon) expressing the cytokine interleukin-12 (IL-12). When inoculated into animals, these ARP adjuvants significantly enhance the humoral and cellular immune responses to immunogenic materials, such as subunit-based vaccines, proteins, antigens expressed by ARPs, or other antigens of interest. It is particularly important to generate a rapid and strong response to a pathogen, for example, a seasonal or pandemic influenza virus.

Experiments showed that VEE-based ARPs, also referred to herein as "VRPs". expressing murine Interleukin 12 (mIL-12) functioned as a highly potent immunological adjuvant when co-administered with antigen-expressing VRPs (e.g. CEA, a tumor-associated antigen from colon cancer cells, and HIV-gag) and HA protein from type A influenza viruses of H3 and H1 serotypes as well as with other protein antigens The optimal required amount of IL-12 ARP, the optimal choice of immune-enhancing cytokine(s) and/or influenza antigens to be included in the ARP adjuvants can readily be determined. Killed, attenuated or subunit-based vaccines can be combined with ARPs expressing IL-12 to elicit functional, protective immune responses against seasonal (H1 and/or H3) as well as potentially pandemic (H5) Influenza viruses as well as any other pathogen of interest. Strong immune responses can also be generated using this same approach of antigen and ARPs expressing IL-12 for other antigens besides those of pathogens.

Alternatively, the immunogenic protein or polypeptide (antigen) can be any tumor or cancer cell antigen which is a protein (or polypeptide). The tumor or cancer antigen can be one expressed on the surface of the cancer cell. Exemplary cancer antigens for specific breast cancers are the HER2 and BRCA1 antigens. Other illustrative cancer and tumor cell antigens are described in S. A. Rosenberg, (1999) *Immunity* 10:281) and include, but are not limited to, MART-1/MelanA, gp100, tyrosinase, TRP-1, TRP-2, MAGE-1, MAGE-3, GAGE-1/2, BAGE, RAGE, NY-ESO-1, CDK-4, β-catenin, MUM-1, Caspase-8, KIAA0205, HPVE&, SART-1, PRAME, p15 and p53 antigens, Wilms' tumor antigen, tyrosinase, carcinoembryonic antigen (CEA), prostate specific antigen (PSA), prostate-specific membrane antigen (PSMA), prostate stem cell antigen (PSCA), human aspartyl (asparaginyl) β-hydroxylase (HAAH), and EphA2 (an epithelial cell tyrosine kinase, see International Patent Publication No. WO 01/12172).

In the methods and compositions provided herein, the immunogenic protein can also be at least one influenza virus immunogenic protein, for example, a hemagglutinin protein, or other protein to which a human produces a protective immune response after administration of an immunogenic composition comprising same. For influenza-derived immunogenic compositions, those which comprise more than one antigenic type, such as the trivalent inactivated influenza vaccine preparations or mixed cocktails of recombinantly produced protein(s), are useful. Other immunogenic proteins can be derived from other viral pathogens, such as measles, mumps, rubella, rubeola, vaccinia, herpesviruses, among others. For prophylaxis for bacterial diseases or intoxications, the immunogenic protein can be (attenuated) anthrax toxins and antigens from *Bacillus anthracis*, antigens from *Yersinia pestis*, inactive diphtheria toxin from *Corynebacterium diphtheriae*, inactive toxin from *Clostridium botulinum*, *Chlamydia* species, *Mycobacterium tuberculosis*, and a host of others known to the art. Protein, glycoprotein, lipoprotein, toxin, attenuated toxin, inactivated toxin, virus, cancer cell antigens, bacterial proteins or portion(s) thereof, inactivated toxins or other bacterial proteins, fungal proteins or portion(s) thereof, attenuated fungus, inactivated fungus, parasite or proteins or portion(s) thereof, protozoan proteins or portion(s) thereof, and the expression product of a minigene encoding a series of epitopes of interest, for example from different influenza virus serotypes, can all be incorporated in the present methods and compositions. In addition, neoplastic cell antigens can be incorporated into the dose sparing vaccine strategies for therapeutic or prophylactic immunizations. Alternatively, the immunogenic protein or polypeptide can be any tumor or cancer cell antigen. The tumor or cancer antigen can be one expressed on the surface of the cancer cell. Exemplary cancer antigens for specific breast cancers are the HER2 and BRCA1 antigens. Other illustrative cancer and tumor cell antigens are described in S. A. Rosenberg, (1999) *Immunity* 10:281) and include, but are not limited to, MART-1/MelanA, gp100, tyrosinase, TRP-1, TRP-2, MAGE-1, MAGE-3, GAGE-1/2, BAGE, RAGE, NY-ESO-1, CDK-4, β-catenin, MUM-1, Caspase-8, KIAA0205, HPVE&, SART-1, PRAME, p15 and p53 antigens, Wilms' tumor antigen, tyrosinase, carcinoembryonic antigen (CEA), prostate specific antigen (PSA), prostate-specific membrane antigen (PSMA), prostate stem cell antigen (PSCA), human aspartyl (asparaginyl) β-hydroxylase (HAAH), and EphA2 (an epithelial cell tyrosine kinase, see International Patent Publication No. WO 01/12172). The immunogenic protein can be a full-length protein or an immunogenic fragment or epitope thereof.

The adjuvant APRs are tested in a nonhuman primate model. In addition to optimization, these studies include monitoring for toxicity and characterization of dose-sparing effects due to ARP adjuvants. For this purpose, existing influenza vaccines such as the trivalent influenza vaccine (TIV) or an inactivated H5 Indonesia vaccine can be used, and functional immune responses to Influenza A strains are measured. The human as well as the simian version of the selected cytokine is cloned and packaged into VRP for use in the analogous subject using the methods provided herein. While human cytokines generally display bioactivity in non-human primates, it is desirable that cytokine be from the same species (e.g., human, Rhesus macaques of Chinese origin) as the immunogenic composition is administered in order to minimize the risk of breaking tolerance against the cytokine itself.

One aspect of the methods and compositions provided herein is the surprising ability of IL-12 expressing ARPs to enhance the magnitude of the humoral, or antibody, responses to a co-administered antigen, however that antigen is delivered. This magnitude can be anywhere from 2 fold to over 100-fold; 5-fold and 10-fold enhancement is typical. Such an enhancement is surprising, given the transient nature of expression and the localized functioning of ARPs, and it is useful in improving vaccine effectiveness and providing high levels of antibodies for collection to use in research, diagnostic and therapeutic applications.

An additional aspect of the methods and compositions provided herein is the ability of IL-12 expressing ARPs to lower the effective immunogenic dose of antigen required in a subject. This ability can be referred to as "dose-sparing", because it allows a given amount of antigen to be used in more patients, thereby sparing the supply of antigen. Dose sparing in which the effective immunogenic dose is between 2 fold and 1000-fold, e.g. 3-fold, 10-fold, 30-fold, 50-fold, 100-fold, 500-fold, have been observed with various antigens in combination with IL-12 expressing VEE replicon particles.

The ability of IL-12-expressing ARPs to lower the effective immunogenic dose required can also provide "boost-sparing", since it can result in fewer administrations required to give an effective immunization of a subject against the antigen. For example, it is common to give an initial dose of a vaccine, and follow that with one or two additional (i.e. "booster") doses over time, e.g. after 1 and 6 months following the initial, i.e. "prime" dose. The use of IL-12 expressing ARPs will allow a reduction in inoculations required, e.g. instead of two booster doses, only one or perhaps no booster is required to achieve the effective dose.

As described herein, high doses of IL-12 expressing ARPs (as compared to the administered antigen) or administering ARPs prior to administering an antigen can result in a suppression of the immune response achieved to certain antigens. This may reflect the immune suppression that has been previously observed with an IL-12 expressing DNA plasmid co-administered with a DNA vaccine (Chen et al. 2001. J. Immunol. 166:7419 and Gherardi et al. 2000. J. Virol. 74: 6278-86), although this effect was not noted by Schadeck et al. The ability to deliver a single dose of IL-12 in a transient manner through the use of ARPs may provide a superior and uniquely effective approach to treat or prevent those disorders in which inappropriately strong immune responses cause disease, e.g. autoimmune disorders, allergy, complications during transplantation such as graft versus host disease, and other immune-system pathologies, such as cytokine burst/storm, delayed type hypersensitivity, immune pathology caused by acute viral infection, and anaphylactic shock.

Another surprising discovery is that IL-12 expressing ARP reduce the level of antibodies to ARP generated in the subject, even while simultaneously enhancing the antibody responses to antigens expressed in the ARP. Thus, the suppression of antibodies to a viral vector is another aspect of the present compositions and methods. Such anti-vector neutralizing antibodies against adenovirus and other types of virus-derived vectors are a serious limitation of current-vectored vaccine strategies, since the vector cannot be used in a subject more than once without a significantly diminished effect. Although VRP vectors appear to be inherently resistant to anti-vector immune responses, the use of ARPs expressing IL-12 could reduce anti-vector responses to ARP and other vectors.

In certain embodiments, the present methods are practiced as part of a heterologous prime-boost immunization strategy, in which the "priming" immunization, comprising the initial administration of one or more antigens to an animal, especially a human patient, in one form (or "modality") in preparation for subsequent administration(s) (often referred to as "boosting") of the same antigen in a different form, or modality. Specifically, the term "priming", or alternatively "initiating" or "activating" an immune response or "enhancing" and "potentiating", defines a first immunization delivering an antigen which induces an immune response to the desired antigen and recalls a higher level of immune response to the desired antigen upon subsequent re-immunization with the same antigen when administered in the context of a different vaccine delivery system (i.e. form or modality). The forms of antigen to be administered can comprise alphavirus vectors, immunogens derived from a pathogen or tumor, recombinant immunogens, synthetic peptides, live, attenuated or killed organisms or extracts thereof, naked nucleic acids, nucleic acids formulated with lipid-containing moieties, pox vectors, adenoviral vectors, herpesvirus vectors, flavivirus vectors, vesicular stomatitis virus vectors, paramyxoviral vectors, parvovirus vectors, papovavirus vectors, and retroviral vectors. The viral vectors can be virus-like particles or nucleic acids. In the methods described herein, the priming step is the administration of a composition that comprises, in addition to an antigen as described above, the IL12-expressing ARP as an adjuvant to the antigen. Following the priming immunization a "boosting immunization", or a "boost", is administered, which is a composition delivering the same antigen as encoded in the priming immunization. The boost is sometimes referred to as an anamnestic response, i.e., an immune response in a previously sensitized animal. Multiple boosts can be administered, utilizing different or the same amounts for each boost. In applying the methods herein to a heterologous prime-boost strategy, the "boosting" immunizations utilize a composition that does not contain the IL-12 expressing VRP. This "boosting" immunization can be referred to as a "heterologous boost" since it is different (in its modality) from the priming immunization.

Influenza rapidly spreads around the world in seasonal epidemics, potentially killing millions of people in pandemic years and hundreds of thousands in nonpandemic years. It creates health care costs with 200,000 hospitalizations in the US and further costs associated with lost productivity. The 20th century saw three influenza pandemics each following a antigenic shift in the hemagglutinin (HA) gene, which killed millions of people (not limited to elderly) all over the world. The world's current major influenza pandemic threat is H5, for which there is no current immunity in the population.

Vaccination remains the most efficient and cost-effective method to protect the public against influenza. Although novel approaches are being explored, vaccines produced using traditional egg-grown killed influenza virus continue to be used. Nevertheless, there are serious shortcomings in the technology, including dependency on eggs, unpredictable immunogenicity and hence dose requirements, risk of producing vaccines against the wrong type of Influenza virus, and risks of insufficient amounts of vaccine doses to protect the public, requiring heavy prioritization for health care officials.

Illustrating the need for improvements, 5-20% of Americans contract influenza every year, causing on average 36,000 deaths during the 1990s, in spite of yearly vaccination efforts. According to CDCP, 218.1 million people in the US will be included in the recommended target groups for vaccination, including 91.2 million with high risk status. The self-reported influenza coverage monitored by the US National Health Interview Survey (NHIS) shows little increase over the past 10 years and has been as low as 24% and 46% for persons with a high-risk status in the age groups 18-49 and 50-65, respectively, and only 40% among health care workers. A higher vaccine coverage would require the manufacture of several times higher numbers of doses than today's capacity can deliver. This situation is even more pressing for a potential pandemic flu where the projection is that a stronger dose will be required, given that they are administered to immunologically naïve persons, which is normally not the case for seasonal influenza vaccinations.

The goal to achieve a population-wide protection against both seasonal and pandemic flu would benefit significantly from a technology that could reduce the amount of antigen per dose and/or if today's vaccines could be elevated to induce a broader immune response. While cellular (CTL) responses may have limited use for protection against infection per se, the literature suggests that CTL responses may have a significant role in protecting against influenza mortality.

The novel adjuvant provided herein has been shown to be highly dose-sparing in preclinical studies. The adjuvant, VRPs expressing IL-12, was found to augment the responses against HA protein to a degree that it reduced the dose of antigen required to elicit high antibody titers by several orders, (e.g. two, three, four or more times) of magnitude. In addition to enhancing the humoral immune response, inclusion of the adjuvant in the vaccine inoculum in the mouse model resulted in significant cellular responses, which are normally not observed with killed virus or subunit protein vaccines.

ARP expressing IL-12 serve as adjuvants for other ARPs expressing useful immunogens. In order to determine if ARPs could be designed to express functional immune-enhancing factors, several different genes encoding cytokines and other immunostimulatory proteins were individually cloned into the replicon DNA plasmid and the transcribed RNAs were packaged into VRP (i.e. "adjuvant VRP"). The procedures used herein for making IL-12 expressing VRP, which are based on a two helper system, are described in detail in U.S. Pat. No. 7,078,218. Specifically, capped replicon RNAs were in vitro transcribed using a T7 RiboMax kit (Promega, Madison Wis.) following the manufacturer's instructions, supplemented with 7.5 mM CAP analog (Promega), from NotI linearized pERK-IL-12 (replicon), capsid helper, and gp helper plasmids. RNAs were purified using RNEasy purification columns (Qiagen, Valencia, Calif.) following the manufacturer's instructions. Vero cells ($1 \times 10^8$ cells) suspended in PBS were combined with 30 µg of replicon, 30 µg capsid helper and 60 µg glycoprotein helper RNA in 0.4 cm electroporation cuvettes and were electroporated using a BIO-RAD Gene Pulser (BIO-RAD). The cells and RNA were pulsed four times with the electroporator set at 580 V and 25 µF. Electroporated cell suspensions were seeded into individual roller bottles containing 150 ml of OptiPro medium (Invitrogen, Carlsbad, Calif.) supplemented with antibiotics and incubated at 37° C. in 5% CO2 for 16-24 h. VRP were harvested and stored in aliquots at −80 C. Titers of the VRP were determined by immunofluorescence assay (IFA) using goat anti-VEE nsP2 specific polyclonal antiserum as the primary antibody and donkey anti-goat Alexa Fluor 488 (Invitrogen) as the secondary antibody on methanol fixed cells using a Nikon Eclipse TE300 fluorescence microscope. Mice were immunized with cocktails containing adjuvant VRPs and VRPs expressing various antigens. Mice were then monitored for humoral responses to the antigen, and cellular responses were measured in spleens obtained by necropsy performed at the end of the studies. Results are summarized in Table 1. Surprisingly, VRP expressing IL-12 were particularly potent in enhancing not only cellular but also humoral responses to the antigen expressed by the VRPs.

TABLE 1

Co-administration of VRP expressing an immunogen with VRP expressing cytokines

| VRP-expressed immunostimulatory factor | VRP-expressed Ag | Enhanced humoral response | Enhanced T-cell response |
|---|---|---|---|
| IL-2 | HIV gag | − | − |
| IL-4 | CEA | − | − |
| IL-4 | HIV gag | − | − |
| IL-12 | CEA | ++ | ++ |
| IL-12 | Flu HA | ++ | ++ |
| IL-12 | HIV gag | ++ | ++ |
| IL-15 | HIV gag | + | − |
| IL-4 + IL-12 | HIV-gag | − | ++ |
| MIP-1α | HIV-gag | − | − |
| MIP-1β | HIV-gag | − | − |

Over 15 immunomodulatory factors were evaluated for their ability to enhance cellular and/or humoral responses to VRP-expressed antigens. Co-delivery of IL-12 VRP consistently resulted in elevated B and T-cell responses to many different expressed antigens including HIV gag, influenza HA (including Wyoming, New Caledonia, Panama, Vietnam), CEA, HSV gD, and Her2; see for example Table 2 and Table 3.

TABLE 2

Effect of IL-12 VRP on Reciprocal Antibody Titer

| Antigen-expressing VRP | IL-12 VRP | Individual Reciprocal Titers | Mean |
|---|---|---|---|
| CEA | none | 20480, 20480, 20480, 20480, 20480, 10240, 10240, 5120, 5120, 2560 | 14482 |
| CEA | $5 \times 10^5$ | >81920*, >81920*, 81920, 40960, 20480, 20480, 20480, 20480, 10240, 5120 | 40960 |
| HA | none | 40960, 40960, 20480, 20480, 20480, 20480, 20480, 10240, 5120, 2560 | 22334 |
| HA | $5 \times 10^5$ | 81920, 81920, 81920 81920, 81920, 40960, 40960, 40960, 20480, 5120 | 63169 |

*For values >81920, the value of the next two-fold dilution value (163840) was used for the GMT computation

TABLE 3

Effect of IL-12 VRP on Reciprocal Antibody Titer

| VRP-expressing CEA | VRP expressing IL-12 | Reciprocal Titer (GMT) |
|---|---|---|
| $5 \times 10^4$ | None | 4305 |
| $5 \times 10^5$ | None | 6241 |

TABLE 3-continued

Effect of IL-12 VRP on Reciprocal Antibody Titer

| VRP-expressing CEA | VRP expressing IL-12 | Reciprocal Titer (GMT) |
|---|---|---|
| $5 \times 10^6$ | None | 17222 |
| $5 \times 10^7$ | None | 34443 |
| $5 \times 10^4$ | $5 \times 10^4$ | 11167 |
| $5 \times 10^5$ | $5 \times 10^5$ | 14482 |
| $5 \times 10^6$ | $5 \times 10^6$ | 31584 |
| $5 \times 10^7$ | $5 \times 10^7$ | 54386 |

Experiments were conducted to compare the adjuvanting effects of IL-12 VRP with that of soluble IL-12. Mice were immunized twice at three-week intervals with $5\times10^5$ IU of CEA-expressing VRPs co-administered with $5\times10^5$ IU of IL-12 VRP, empty VRP, or with soluble IL-12 protein at 1 ng, 10 ng, or 100 ng per dose. Immunological responses were measured by CEA-specific ELISA (humoral responses) at one week after the second immunization (i.e. "post-boost"), and by ELISPOT (cell-mediated responses). IL-12 VRP was significantly more potent in elevating cell-mediated responses to CEA than soluble recombinant IL-12 at either dose tested. Although the mechanism for the superior nature of IL-12 VRP was not studied, and without wishing to be bound by any particular theory, it is believed that the tropism of VRPs to the lymph nodes results in IL-12 expression directly at a site where presentation of antigen for the induction of T-cell responses is known to occur.

Adjuvanting Activity of VRP Expressing Interleukin 12 for Protein-Based Immunogens The immune-enhancing activity of IL-12 expressing VRP ("IL-12 VRP") can also be employed in combination with non-ARP vaccines, e.g. protein vaccines. Mice were immunized twice subcutaneously with a low-dose of $HA_{Wyoming}$ protein alone or in combination with IL-12 VRP. At three weeks following the first immunization (i.e. "post-prime"), the humoral responses to HA were significantly higher in sera from the group that received protein combined with IL-12 VRP than in mice immunized with protein alone. Even two immunizations with protein alone resulted in reciprocal ELISA titers that were significantly lower than the titers elicited after only a single immunization using IL-12 expressing VRP. In stark contrast, empty VRP, i.e. VRP in which the replicon does not express any heterologous sequence, elevated the humoral anti-HA responses slightly, but only to a significantly lower level than IL-12 expressing VRP. It was previously shown that the empty VRP adjuvanting effect is based on signaling though IFN α/β whereas IL-12 is known to stimulate cells in the lymph node to secrete IFN-γ. This indicates that expressing IL-12 at the same site as the antigen has additional immunostimulatory effects.

Adjuvant VRPs Expressing IL-12 Result in Enhanced T Cell Immune Responses

Figure 1A:
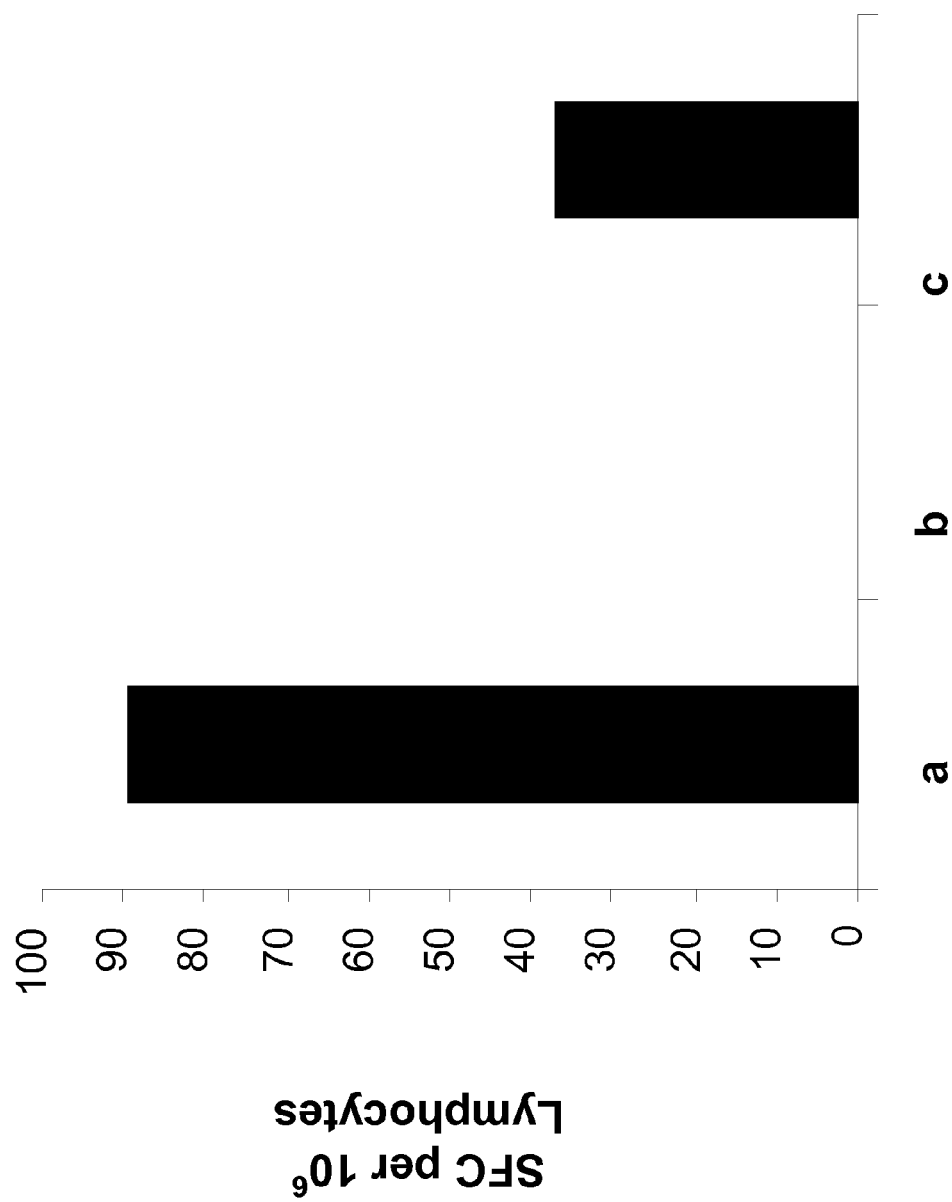
FIG. 1 demonstrates that IL12-VRPs co-administered with multiple proteins, enhance cellular immune responses. Cellular responses to $HA_{Wyoming}$, $HA_{New\ Caledonia}$, and HSV gD, are presented in FIGS. 1A, 1B, and 1C, respectively. Balb/c mice were immunized with either of mentioned recombinant proteins or the three combined, as follows: (a) IL-12 VRP+ 100 ng recombinant protein; (b) 100 ng recombinant protein mixture (all three proteins combined); (c) IL-12 VRP+100 ng recombinant protein mixture)
Figure 1B:
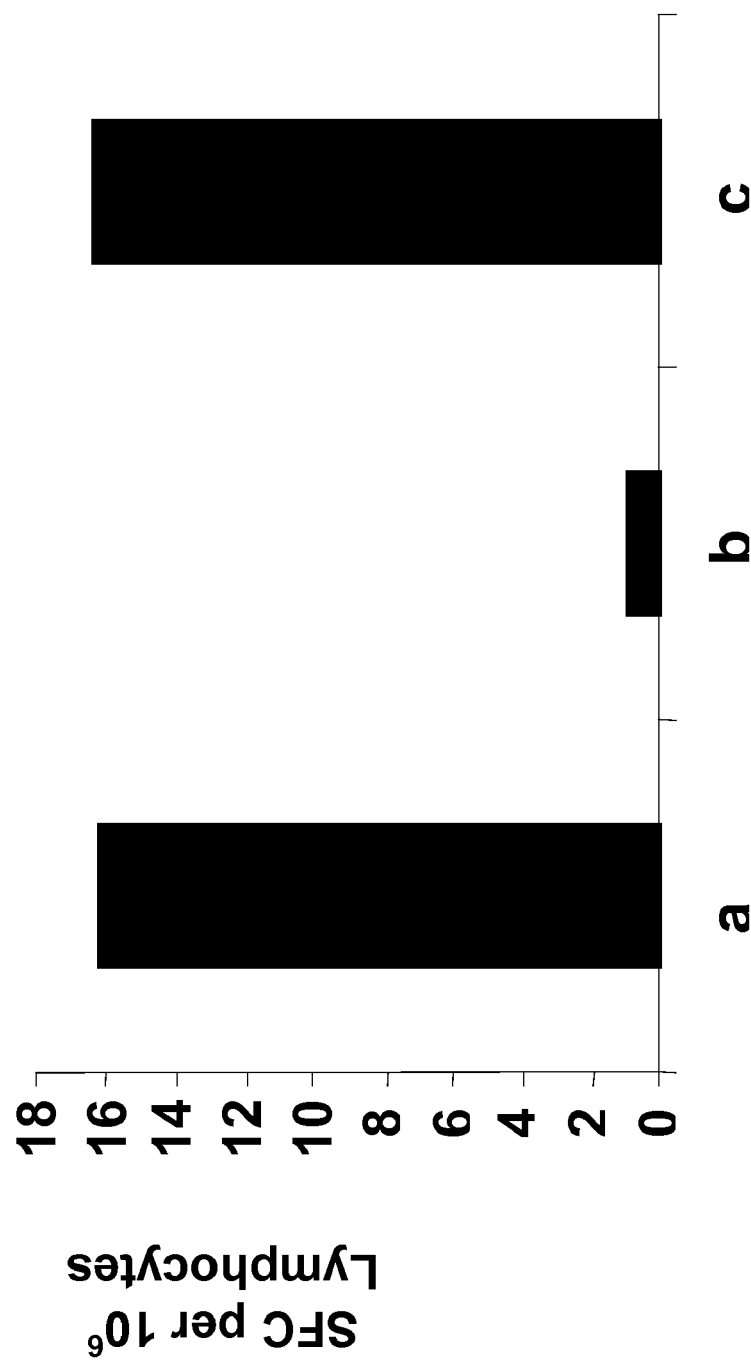
Figure 1C:
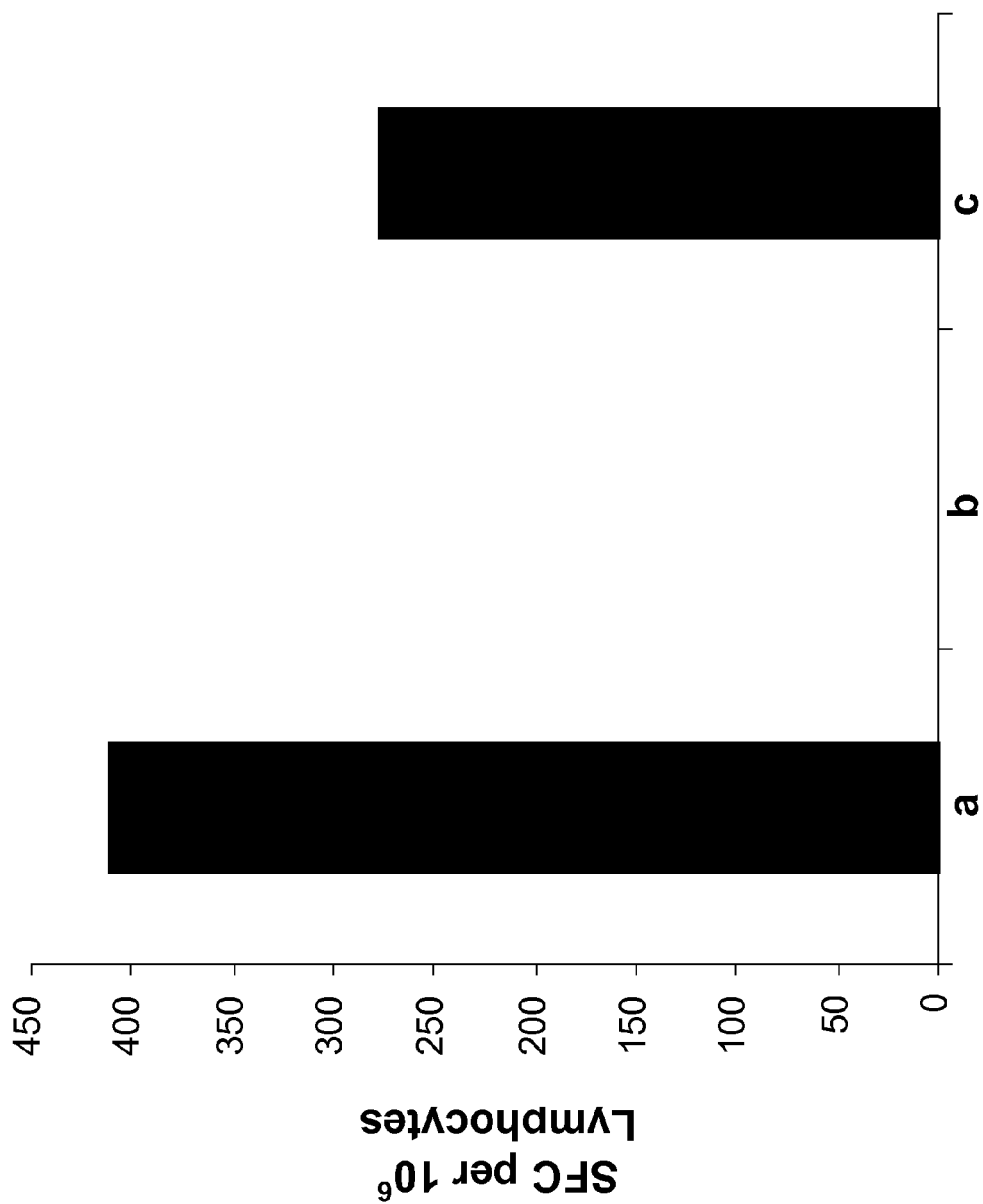
Figure 2:
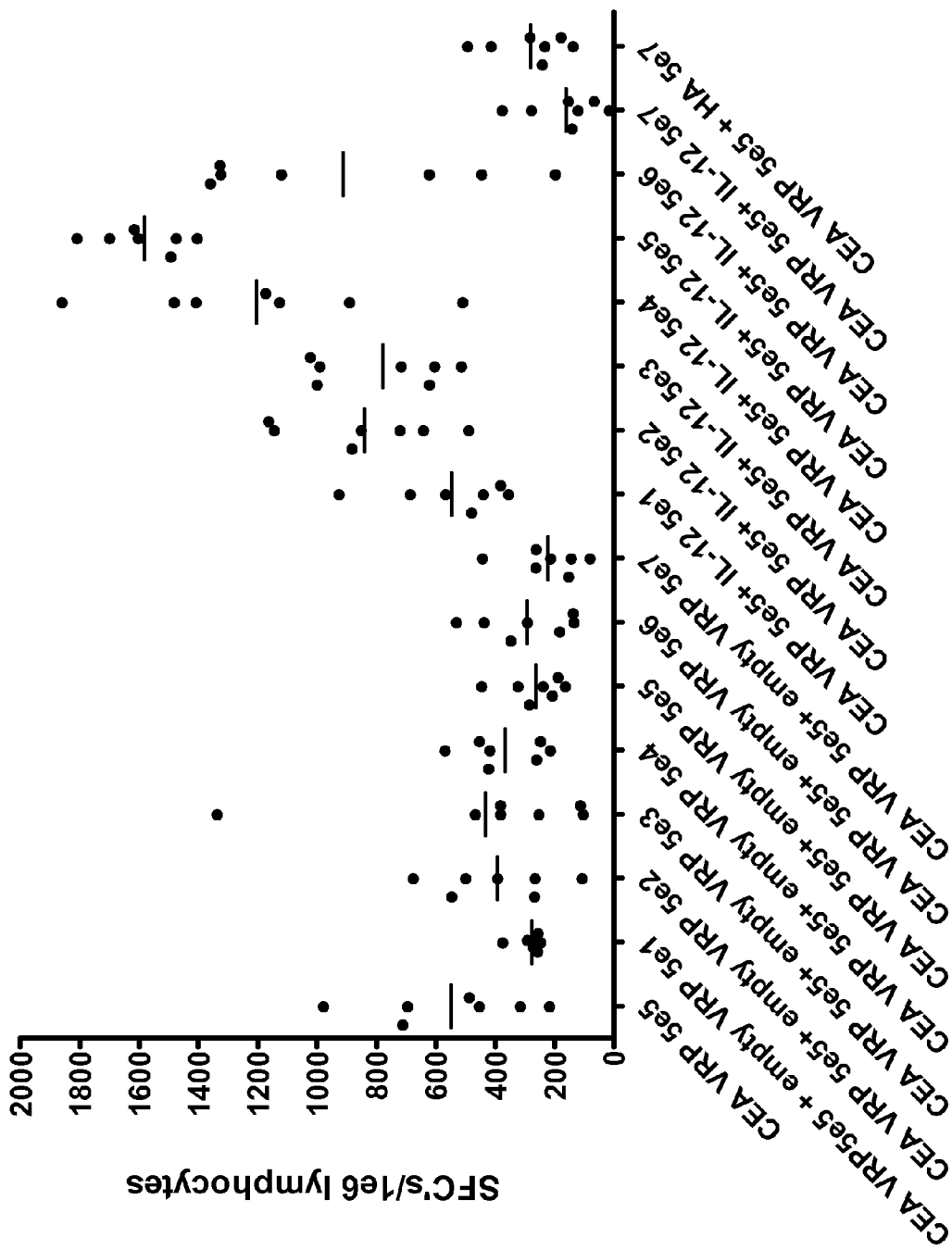
FIG. 2 illustrates that IL-12 VRP enhance cellular responses to VRP expressed antigens. Cellular responses in mice immunized with a constant dose ($5 \times 10^5$ infectious units, IU) of CEA VRP alone or in combination with increasing doses of "empty" VRP (no foreign gene inserted), VRP expressing an irrelevant immunogen (HA), or IL12 VRP, as indicated. The doses used range from $5 \times 10^1$ to $5 \times 10^7$, as indicated. Titration experiments showed that the optimal enhancement of cellular responses to a dose of $5 \times 10^5$ infectious units (IU) CEA VRP was achieved when using $5 \times 10^5$ IU IL-12 VRP.
Figure 3:
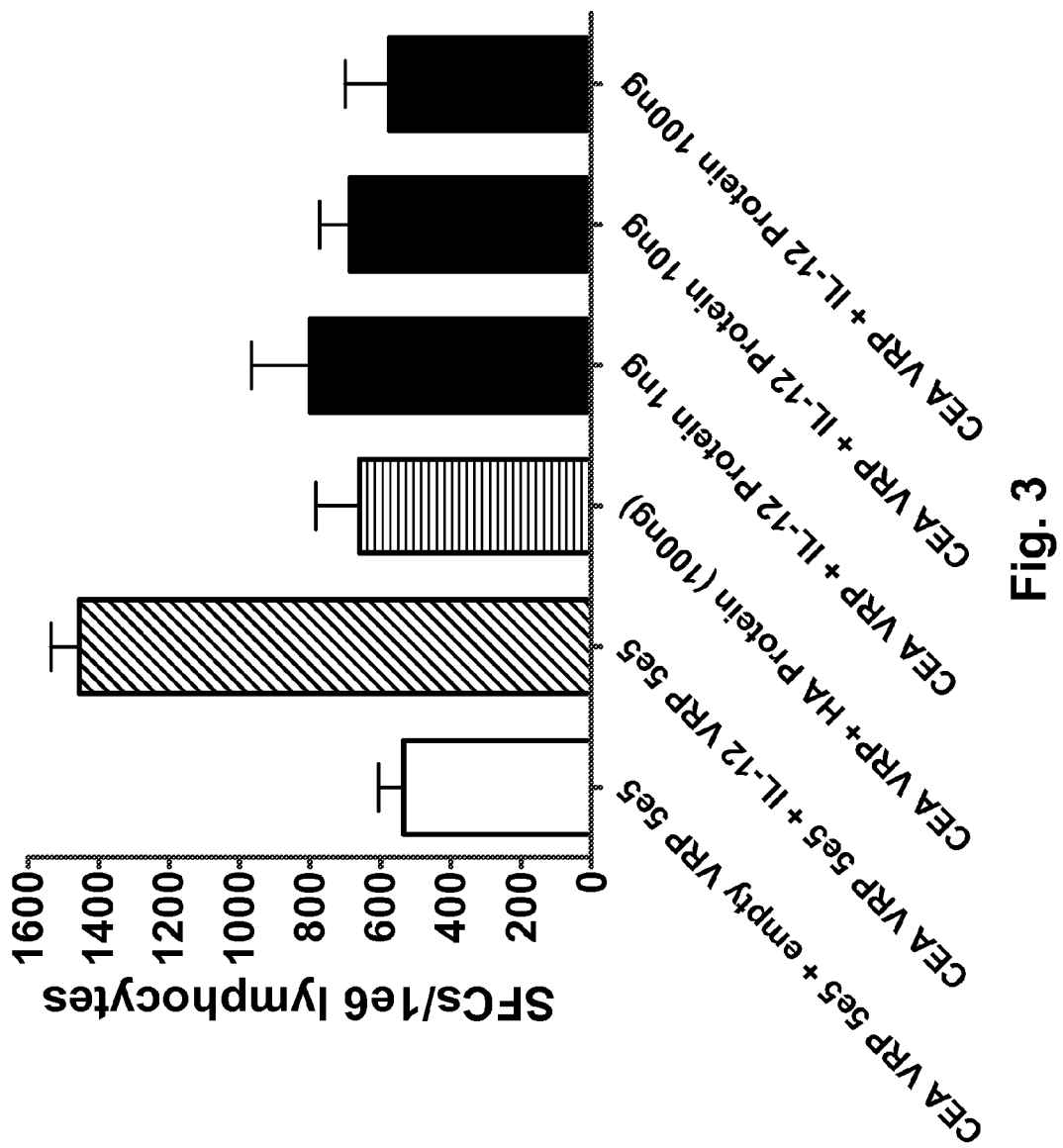
FIG. 3 provides a comparison between the adjuvant effects of soluble IL-12 and IL-12 VRP in terms of CEA-specific cellular responses to CEA VRP. Groups of 8 Balb/c mice were immunized subcutaneously at week 0 and week 3 with $5 \times 10^5$ IU of CEA VRP in combination with IL-12 VRP or soluble recombinant IL-12 (1-100 ng). Control groups received CEA VRP in combination with empty VRP or with 100 ng of irrelevant protein (HA), as indicated. Serum samples and spleens were obtained at one week post-boost for the analysis cellular responses.
Figure 4A:
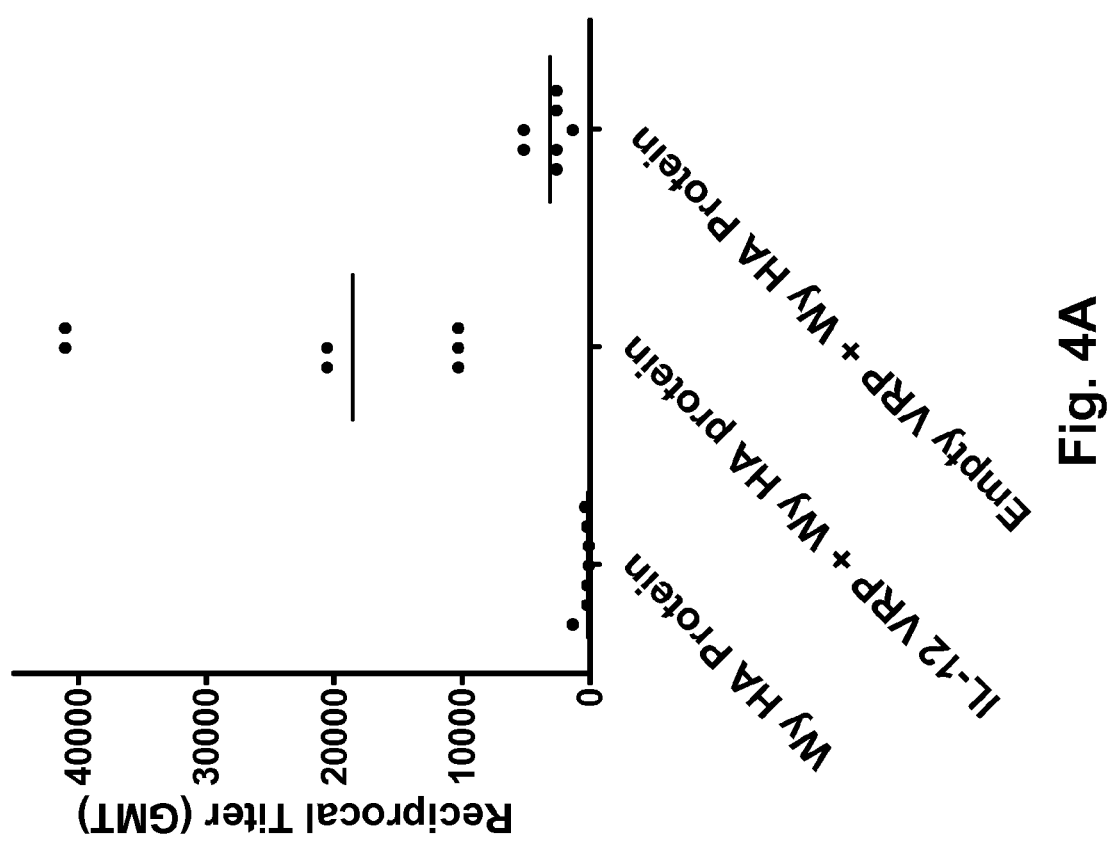
FIGS. 4A-4C demonstrate that IL-12 VRP enhances the humoral and cellular responses to a low-dose immunization of HA protein. Mice were immunized with 100 ng of recombinant $HA_{Wyoming}$ either alone, in combination with empty VRP at $5 \times 10^5$ IU per dose or with IL-12 VRP at $5 \times 10^5$ IU per dose. Humoral responses were measured in sera obtained at one day before the boost (FIG. 5A) or one week after the boost (FIG. 5B). Cellular responses (FIG. 5C) were measured by ELISpot using a library of overlapping peptides spanning the whole HA amino acid sequence.
Figure 4B:
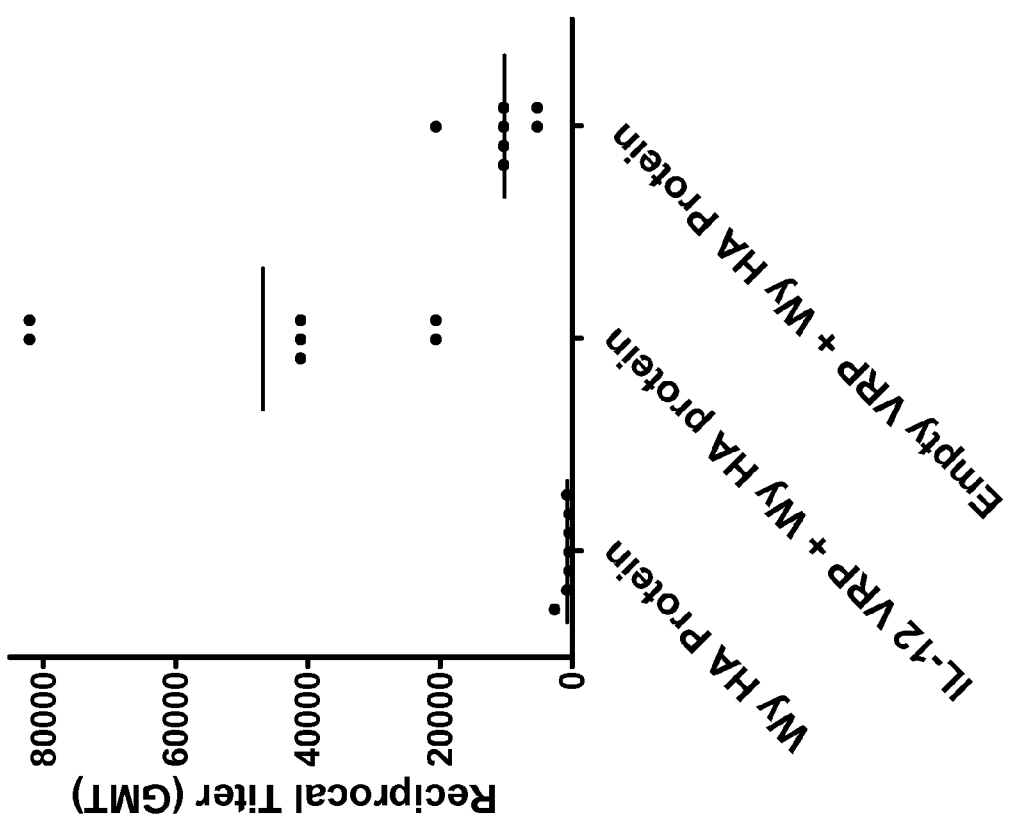
Figure 4C:
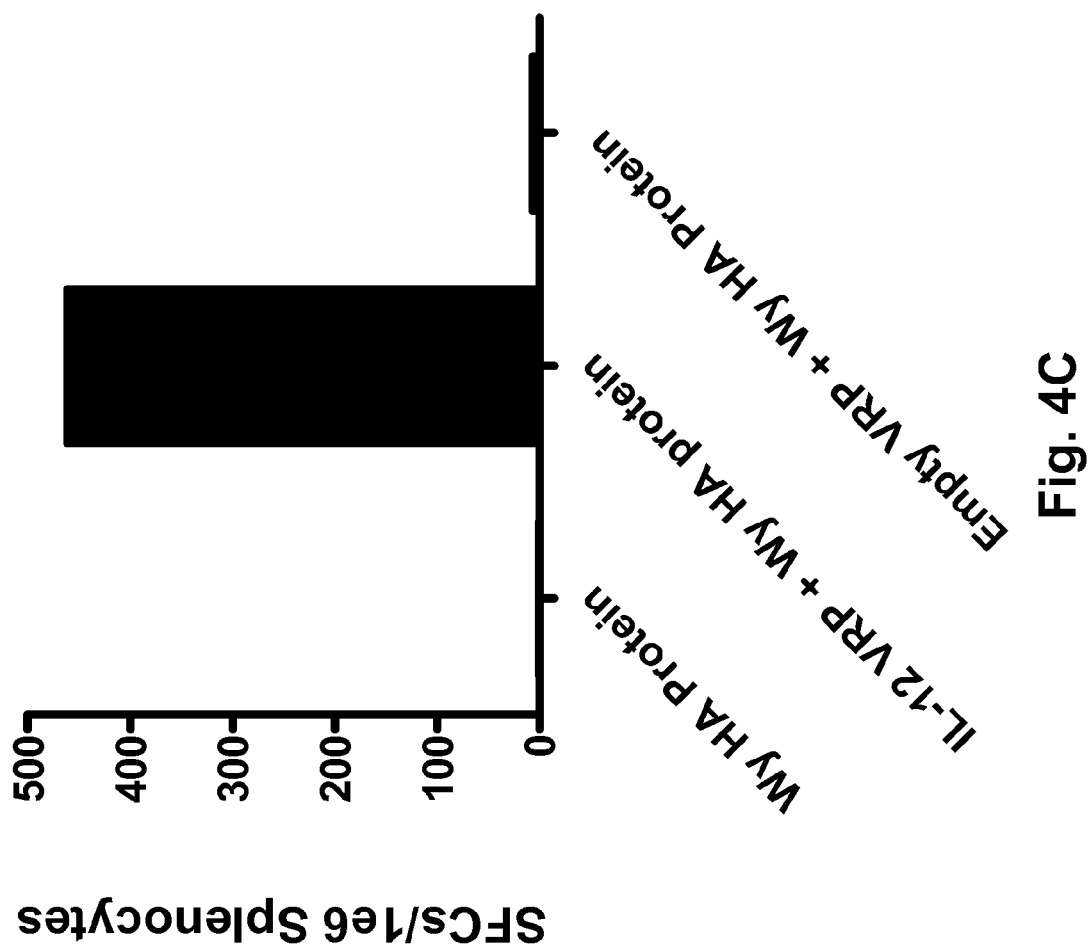

The effect of IL-12 VRP on induction of T cell responses to co-administered protein antigens was analyzed. Mice immunized twice with (a) protein alone or (b) protein mixed with IL-12 VRP were sacrificed at one week after the second immunization (i.e. "post-boost"). Similar to the humoral responses, there was a significant adjuvanting effect achieved by including the IL-12 VRP component in the vaccine. Proteins are normally extremely poor as T cell immunogens. HA is no exception as no SFCs were detected in our ELISpot assay. However, by including $5\times10^5$ IU of IL-12 VRP, strong antigen-specific cellular responses were detected. The difference was dramatic (1 versus 462 SFCs per million lymphocytes) (FIG. 4C], thus essentially transforming a soluble recombinant protein into a potent T-cell inducing vaccine. To our knowledge this is the most potent adjuvant known for eliciting T-cell responses against inoculated protein in solution.

IL-12 VRP as a Dose-Sparing and Boost-Sparing Adjuvant

In addition to being a useful immune-enhancing and T-cell inducing adjuvant, experiments have demonstrated the utility of IL-12 VRP for dose-sparing in protein-based influenza vaccination. Groups of Balb/c mice were immunized with recombinant $HA_{Wyoming}$ at doses varying from 1 ng to 1 µg. The groups were further split in two in a way that half of the animals also received $5\times10^5$ IU of IL-12 VRP adjuvant. Protein alone elicited antibody ELISA mean titers ranging from 30 to about 500 at three weeks after the first, or "prime" inoculation, whereas a booster immunization increased the titers up to about 3100 GMT at the higher doses of protein. However, including IL-12 VRP in the vaccines significantly enhanced the HA-specific antibody titers. For all doses tested, one immunization of protein combined with IL-12 VRP resulted in stronger humoral responses than two immunizations with protein alone. This indicates that the IL-12 VRP adjuvant had a "boost-sparing" effect on the protein vaccine. By comparing the ELISA titers between the groups receiving escalating doses it was apparent that similar or higher humoral responses could be elicited using at least 100 to 1000 times less protein antigen when used in combination with IL-12 VRP adjuvant, indicating a significant dose-sparing effect. Indeed, a single immunization with 10 ng of protein combined with IL-12 VRP resulted in mean ELISA titers of about 3600, significantly higher than mice immunized twice with 1000 ng of protein alone, indicating a dose-sparing as well as a boost-sparing role of the adjuvant.

Optimal doses of IL-12 expressing VRPs were determined by immunizing mice with a fixed, low dose (e.g. 100 ng) of recombinant $HA_{Wyoming}$ protein. The protein vaccines were formulated together with IL-12 VRP at different doses ranging from 5e3 to 5e7 IU. Humoral and cellular responses were measured as for the experiment described above. Even the smallest dose of IL12 VRP provided a detectable adjuvant activity: antibody titration showed that by including 5e4 IU of IL-12 VRP the humoral responses were increased by about one order of magnitude. Interestingly, the adjuvant activity for humoral responses peaked at 5e5 IU of IL-12 VRP as 5e6 IU did not perform stronger than 5e5 IU, and co-administration of 5e7 IU of IL-12 VRP resulted in humoral responses that were significantly lower than using 5e5 IU. This experiment indicates that dose-escalation studies should be performed for determining optimal doses of the adjuvant for each host species and possibly for each protein vaccine. The cellular immune responses were increased in a more typical dose-response behavior. Including 5e4 IU of IL-12 VRP increased the number of spot-forming cells from 2.5 to 55.3 per 1e6 lymphocytes. Gradually increasing the dose of adjuvant further at ten-fold increments augmented the number of SFCs correspondingly with no obvious peak or plateau.

Use of IL-12 ARP as a Universal Adjuvant to Multivalent Protein Vaccines

Many vaccines are formulated as multivalent preparations, and IL12 expressing ARP can be used to adjuvant these preparations. Four different recombinant proteins ($HA_{Wyoming}$, $HA_{New\ Caledonia}$, CEA, and HSV gD) were used either alone or in a tetravalent cocktail to immunize Balb/c mice. The groups were further divided into mice receiving IL-12 VRP or diluent only as adjuvant. ELISA was used to measure humoral responses to three of the components in order to evaluate possible cross-inhibitory or saturating effects between the protein antigens. As expected, the antibody titers to $HA_{Wyoming}$ were significantly higher in sera from mice that had also received IL-12 VRP than in mice receiving $HA_{Wyoming}$ only.

Figure 9A:
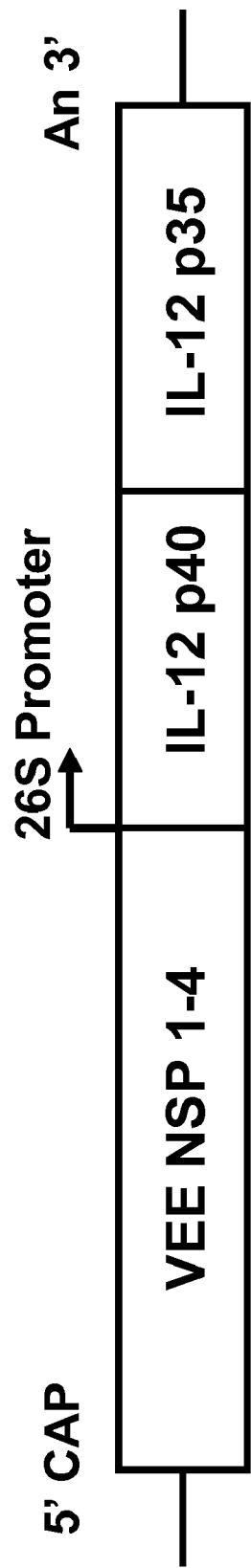
FIGS. 9A-9B show expression of murine IL-12 from a VEE replicon vector.
Figure 9B:
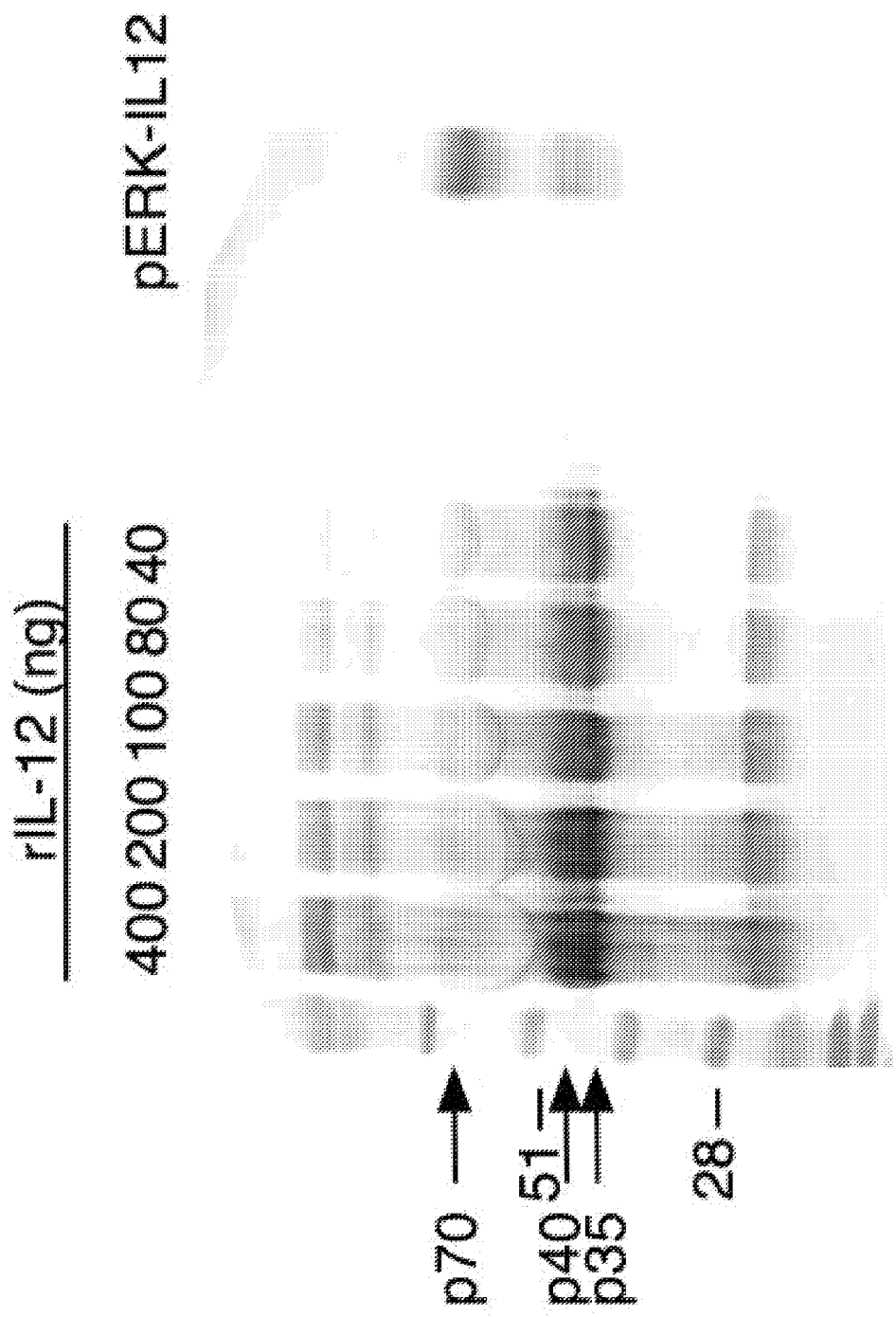
Figure 10:
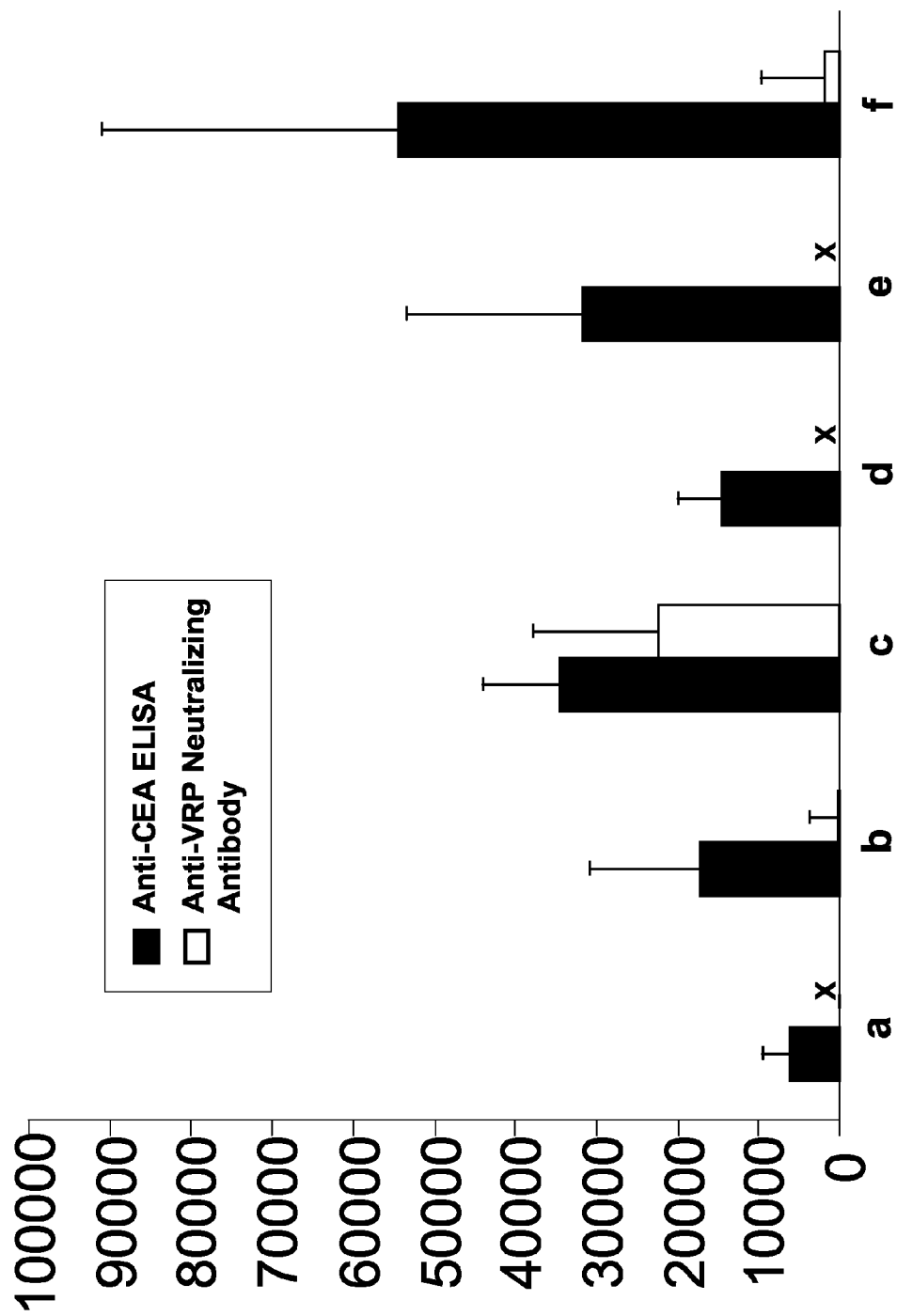
FIG. 10 shows that humoral responses to the VRPs themselves ("anti-VRP neutralizing antibody") are not increased by IL-12 ARPs. Mice were immunized with CEA VRP or CEA in combination with IL-12 VRPs: (a) $5 \times 10^5$ CEA VRP; (b) $5 \times 10^6$ CEA VRP; (c) $5 \times 10^7$ CEA VRP; (d) $5 \times 10^5$ CEA VRP+$5 \times 10^5$ IL-12 VRP; (e) $5 \times 10^6$ CEA VRP+$5 \times 10^6$ IL-12

Mice were immunized once or twice with either a tetravalent mix (gD, New Cal HA, CEA, and Wyoming HA) or with the same mix also including IL-12 VRP (see FIG. 9 and Table 4). The data show that IL-12 VRP served as an adjuvant for humoral responses to specific protein components (New Cal HA, Wyo HA, gD) when presented as part of a cocktail. Thus, it is possible to use IL-12 VRP to adjuvant complex mixtures of immunogens, such as lysates or inactivated virus preparations. It is important that the antigenic preparations used in the present methods and compositions be prepared correctly to preserve native conformations.

TABLE 4

Effect of IL-12 VRP on Reciprocal Antibody Titer

| Recombinant Protein | IL-12 VRP (IU) | Mean Reciprocal Titer (GMT) |
|---|---|---|
| Wyoming HA 100 ng | none | 285 |
| Wyoming HA 100 ng | $5 \times 10^5$ | 36,491 |
| WyHA/NCHA/CEA/gD* | $5 \times 10^5$ | 25,803 |
| New Caledonia HA 100 ng | none | 80 |
| New Caledonia HA 100 ng | $5 \times 10^5$ | 12,902 |
| WyHA/NCHA/CEA/gD* | $5 \times 10^5$ | 2,032 |
| HSV gD 100 ng | none | 2874 |
| HSV gD 100 ng | $5 \times 10^5$ | 11,494 |
| WyHA/NCHA/CEA/gD* | $5 \times 10^5$ | 8,127 |

*A protein mix consisting of 100 ng of each protein was used

Mechanisms of Action for VRP-Based Adjuvants

Without wishing to be bound by any particular theory, the inventors believe that increased amounts of IL-12 expressed directly at the site of antigen presentation serves to elevate the $T_H1$ type responses. Interleukin 12 is known to differentiate naïve CD4 into $T_H1$-like cells, which generally have the effect for the humoral response to drive plasma cells to undergo immunoglobulin isotype-switching for the production of IgG2a in mice. This is in contrast to TH2 type responses which correlate by a dominance of IgG1. By using secondary antibodies specific for both isotypes we were able to measure the reciprocal ELISA titers of antigen-specific IgG1 as well as IgG2a. Mice were immunized with recombinant Wyoming HA either intraperitoneally or subcutaneously alone or in combination with either empty VRP or IL-12 VRP. When sera were analyzed for their IgG isotype profiles it was not surprising to see that protein alone induced predominantly IgG1, consistent with a $T_H2$ type response. Co-administering IL-12 VRP resulted in greatly increased overall antibody responses, but shifted the profile to a predominantly IgG2a response. The IgG isotype profile shifted to IgG2a dominance when a low dose of protein was administered SC but not when a large dose was given IP. Empty VRP used as an adjuvant elevated the IgG responses modestly but did not alter the IgG1/IgG2a balance. This is consistent with the findings in Thompson et al, (2006) PNAS 103:3722-3227 where cell-mediated responses were not dramatically enhanced by co-administering empty VRP. In contrast, the IL-12 VRP adjuvant resulted in greatly enhanced T cell responses.

The effect of IL-12 expressing VRP may be most advantageous during the priming, or the first immunization, when a multiple dose vaccine regimen is used. Thus, it is comtemplated that a vaccine composition may comprise: (1) an initial, priming injection that contains IL-12 VRP and an antigen preparation, and (2) one or more boosting injections that contain only an antigen preparation (i.e the same antigen delivered in the same preparation or in a different preparation, e.g. recombinant protein and antigen-expressing VRP). For example, in FIGS. 11-14, when IL-12 VRPs were used to adjuvant responses to the current influenza vaccine, "TIV", the right-most bar on each graph shows the significant enhancement of both humoral and cellular responses after the first, or priming, administration.

VRP vaccines were previously found to direct the expression of the gene of interest to the draining lymph node, which also is the site where antigen presentation to naïve T cells occurs. IL-12 acts by stimulating T-cells to proliferate. By providing IL-12 expression at the same site (likely the same lymph nodes) where the antigen is being processed and presented, it is likely that higher immunostimulatory effects can be achieved than those obtained by administration of soluble IL-12 protein, which would be expected to have a high diffusion rate, thus effectively reducing the local concentration at the relevant bio-compartment. IL-12 VRP had a significantly stronger adjuvant effect than co-administration of recombinant IL-12 protein. Interestingly, while IL-12 VRP had a clear adjuvant activity when co-administered together with protein, the effect was not observed when IL-12 VRP was administered at the same time as the protein but in the contralateral foot pad, further indicating that the stimulatory effect of IL12 expressing VRP is a locally mediated effect. Tissue PCR experiments showed that VRP expression of the gene of interest continues for a few days until the expressing cell succumbs. While soluble protein rapidly disappears by degradation as well as diffusion, VRP-expressed cytokines are produced locally during the course of the antigen presentation process in a manner mimicking the kinetics observed when IL-12 is produced by dendritic cells and macrophages during primary virus infection. It can be suggested that using soluble IL-12 for boosting immune responses to the same degree as IL-12 VRP would require much higher systemic doses, with higher consequent reactogenicity. An alternative to IL-12 VRP would be to express IL-12 from a DNA vector that could be administered by needle injection, an approach that has been explored (Schadeck et al. 2006. Vaccine 24:4677-4687; Chen et al. 2001. J. Immunol. 166:7419-7426). However, DNA vectors may target different sites and the prolonged expression following DNA delivery could be problematic in the sense that persistent expression after antigen presentation may lead to bystander activation of naïve T-cells or proliferation of autoreactive T cells. VRP-mediated expression, on the other hand, is transient and since there is no DNA stage in the alphavirus replicon cycle, there is no risk of integration.

The optimal dose for a given subject and a given disease target is easily determined based on the teachings herein. A range of ARPs expressing IL12, say from $10^2$ to $10^8$, can be tested in combination with the immunogen. The optimal dose for enhancing cellular responses may not always be the optimal dose for enhancing humoral responses; if both responses are desired, it is advantageous to test several concentrations of IL12-ARPs within the range given to determine the optimal overall immune response. Preferably, when expressing the immunogen from an ARP, the dose of IL12-ARP co-administered with the immunogen expressing ARP does not exceed the immunogen-expressing ARP dose, and it is typically the same dose.

Optimizing the Use of VRP Adjuvants in Non-Human Primates

VRPs are tested in a nonhuman primate model. In addition to optimization, these studies include monitoring for toxicity and characterization of dose-sparing effects due to VRP adjuvants. For this purpose, existing influenza vaccines such as the trivalent influenza vaccine (TIV) or an inactivated H5

Indonesia vaccine are used and functional immune responses to Influenza A strains are measured. The human as well as the simian version of IL-12 is cloned and packaged into VRPs for the further studies. While human cytokines generally display bioactivity in non-human primates, these experiments utilize cytokines from the same species (Rhesus macaques of Chinese origin) in order to minimize the risk of breaking tolerance against the cytokine itself.

Evaluation of Adjuvant Activity of IL-12 VRP in Non-Human Primates

Groups of four animals (Rhesus macaques) are immunized with 3 doses of inactivated influenza vaccine with and without the co-administration of adjuvant VRP.

TABLE 5

Experimental Design for Animal Studies

|  | 1 | 2 | 3 | 4 | 5 | 6 | Animals |
|---|---|---|---|---|---|---|---|
| Inactivated influenza vaccine | 15 ug | 1.5 ug | 0.15 ug | 15 ug | 1.5 ug | 0.15 ug | |
| Adjuvant VRP | | | | 1e7 | 1e7 | 1e7 | |
| No animals | 4 | 4 | 4 | 4 | 4 | 4 | 24 |
| Total | | | | | | | 24 |

Optimization for Amount of IL-12 VRP Required in Non-Human Primates to Achieve at Least a 10-Fold Dose-Sparing Adjuvant Activity Groups of four animals (Rhesus macaques) are immunized with a fixed dose of inactivated H5 influenza/Indonesia and be co-administered with IL-12 VRP at different doses. The exact dosage used is between about 1 and 100 µg, desirably between 1 and 15 µg.

TABLE 6

Experimental Design for Animal Studies

|  | 1 | 2 | 3 | 4 | 5 | 6 | Animals |
|---|---|---|---|---|---|---|---|
| Inactivated influenza vaccine | 15 ug | 1.5 ug | 1.5 ug | 1.5 ug | 1.5 ug | 1.5 ug | |
| Adjuvant VRP | | | 1e5 | 1e6 | 1e7 | 1e8 | |
| No animals | 4 | 4 | 4 | 4 | 4 | 4 | 24 |
| Total | | | | | | | 24 |

Figure 5:
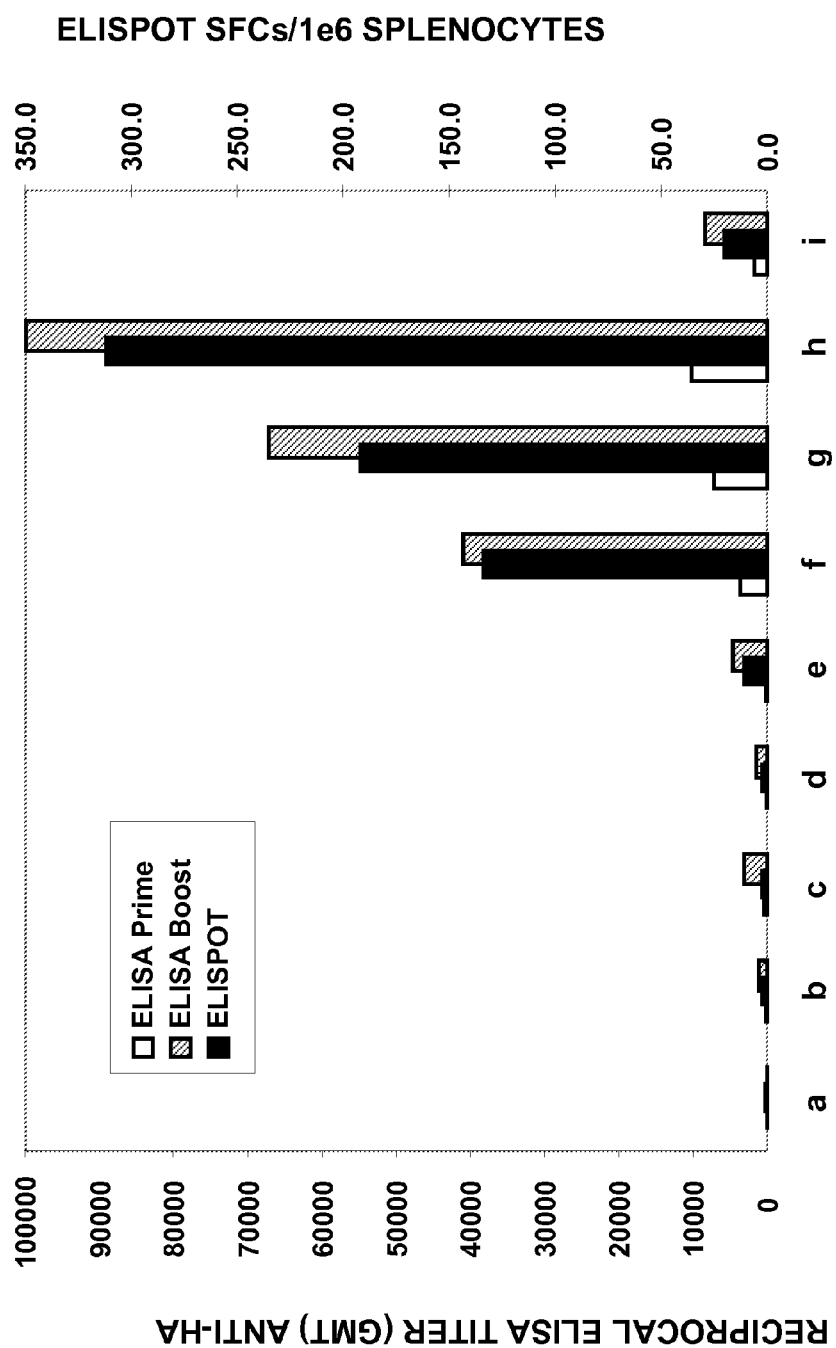
FIG. 5 shows the dose-sparing activity of IL-12 VRP adjuvant for recombinant HA vaccines. Groups (a)-(d) (of 6 Balb/c mice each) were immunized in the foot pad at week 0 and 3 with escalating doses of baculovirus-expressed HAWyoming ("rec HA") obtained from Protein Sciences, Inc.: (a) 1 ng rec HA; (b) 10 ng rec HA; (c) 100 ng rec HA; (d) 1000 ng rec HA. Groups (e)-(h) received the same increasing doses of rec HA but mixed with $5 \times 10^5$ IU of IL-12 VRP: (e) 1 ng rec HA+$5 \times 10^5$ IU IL-12 VRP; (f) 10 ng rec HA+$5 \times 10^5$ IU IL-12 VRP; (g) 100 ng rec HA+$5 \times 10^5$ IU IL-12 VRP; (h) 1000 ng rec HA+$5 \times 10^5$ IU IL-12 VRP. Serum samples were analyzed for HA-specific IgG by ELISA with samples taken at the time just prior to boost (open bars) and one week post-boost (hatched bars). The Elisa plates were coated with the same recombinant protein that was used for the immunogen. For assaying cellular responses spleens were collected at 1 week post-boost and splenic lymphocytes were assessed for HA—specific T cells using interferon gamma ELISPOT assays and a pool of overlapping HA—derived peptides. The number of SFCs/1e6 cells was determined and graphed (solid black bars, secondary Y-axis). The control group (i) received $5 \times 10^5$ IU empty VRP+100 ng rec HA.
Figure 6:
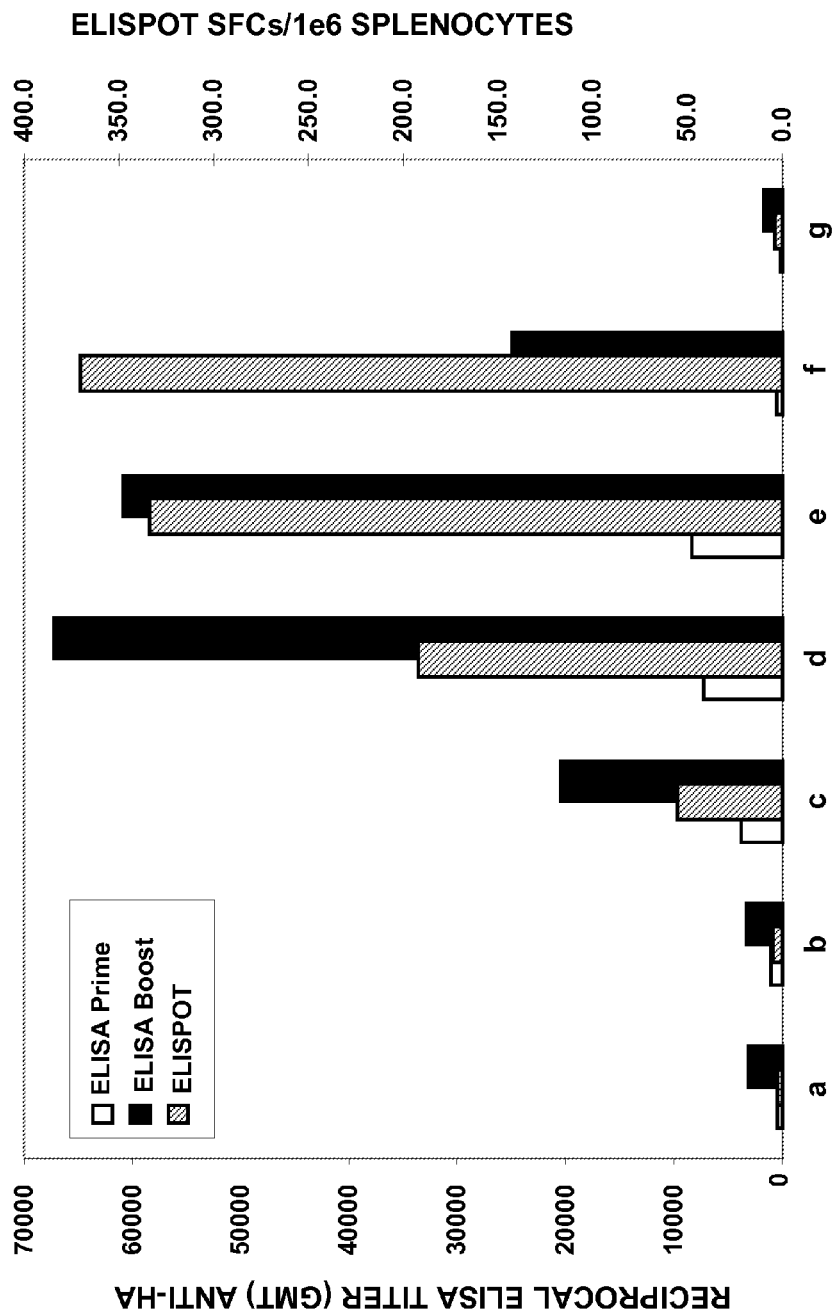
FIG. 6 illustrates the dose requirement for adjuvant activity of IL-12 VRP. Mice were immunized with 100 ng of recombinant HA protein complemented with IL-12 VRP at ten-fold increasing doses ranging from $5 \times 10^3$ to $5 \times 10^7$ IU: (a) 100 ng recombinant HA; (b) 100 ng recombinant HA+$5 \times 10^3$ IU IL-12 VRP; (c) 100 ng recombinant HA+$5 \times 10^4$ IU IL-12 VRP; (d) 100 ng recombinant HA+$5 \times 10^3$ IU IL-12 VRP; (e) 100 ng recombinant HA+$5 \times 10^6$ IU IL-12 VRP; (f) 100 ng recombinant HA+$5 \times 10^7$ IU IL-12 VRP. Humoral and cell-mediated immune responses were measured, see the FIG. 6 legend for experimental details. One group of mice was immunized with $5 \times 10^5$ IU of IL-12 VRP in the left footpad whereas the recombinant HA protein was administered by a separate needle injection into the right footpad (g).
Figure 7:
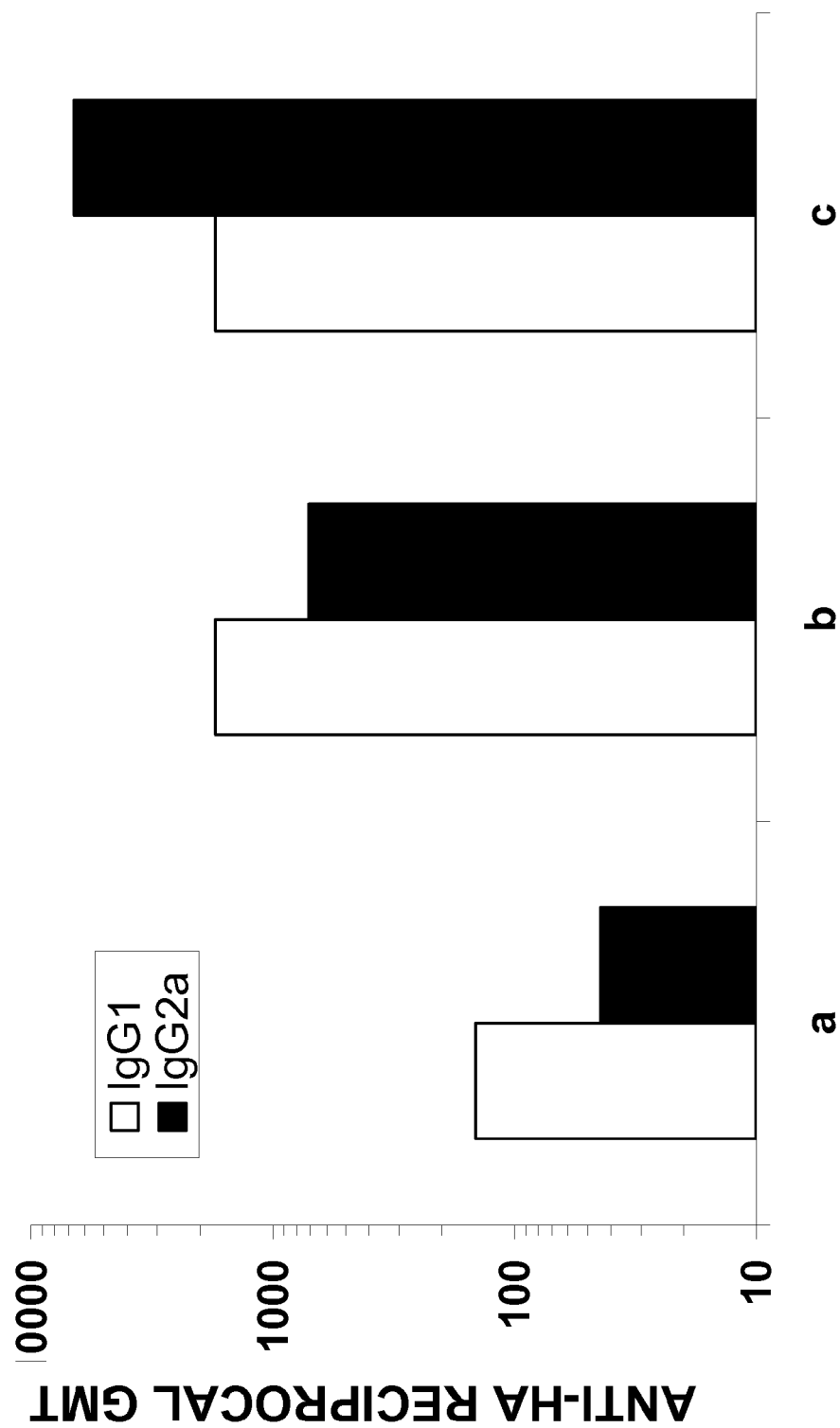
FIG. 7 illustrates IgG isotype profiling following subcutaneous immunization of mice with HA protein in combination with VRP adjuvants. (a) 100 ng recombinant HA protein; (b) 100 ng recombinant HA protein+$5 \times 10^5$ "empty" VRP; (c) 100 ng recombinant HA protein+$5 \times 10^5$ IL-12 VRP.
Figure 8:
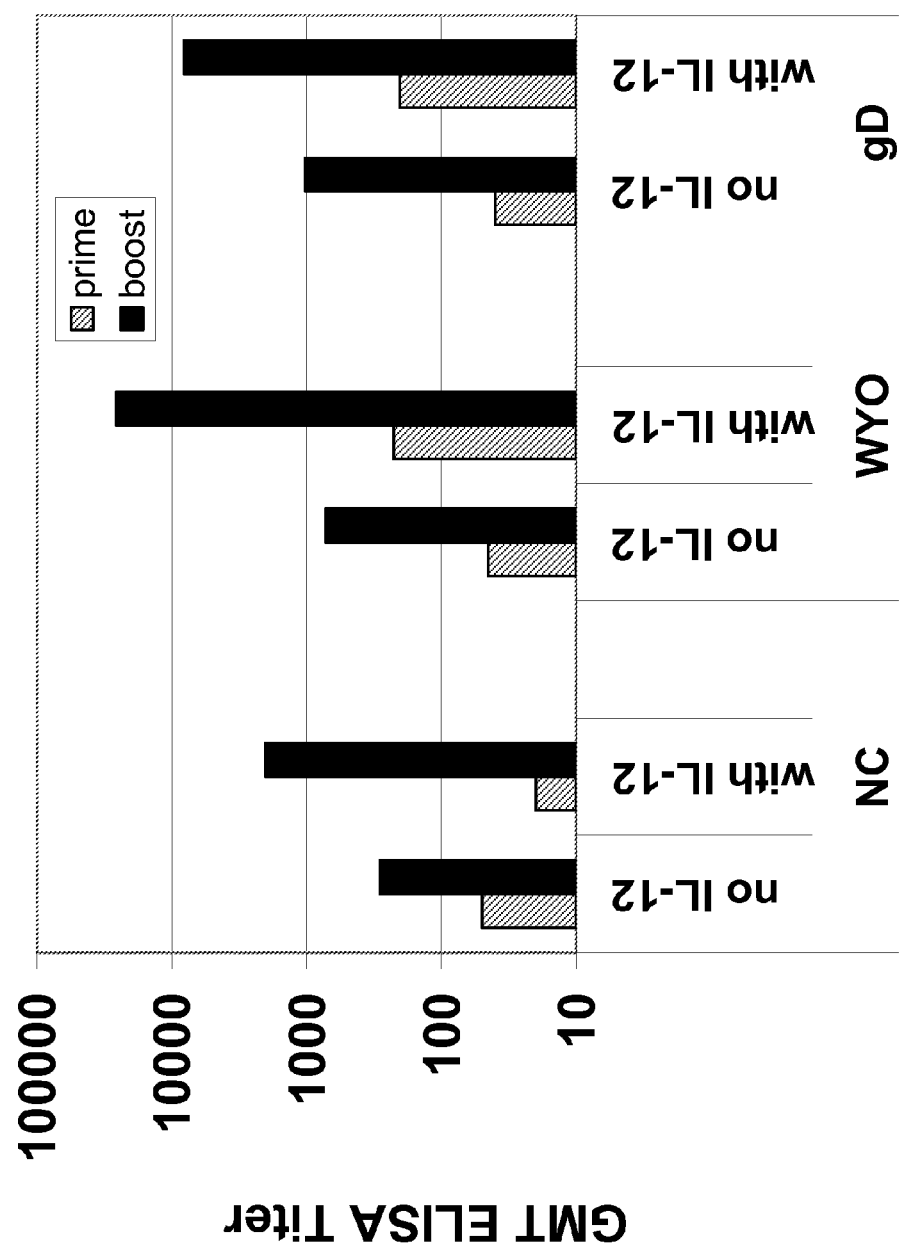
FIG. 8 shows the antigen-specific antibody titers after prime (left bar in pair) and boost (right bar in pair) with a protein antigen cocktail (New Caledonia HA, Wyoming HA, HSV gD) with or without ARPs expressing IL-12.

Optimization and Characterization of the Effect of IL-12 VRP as Dose-Sparing Adjuvants for Seasonal Influenza Vaccines in Mice HA baculovirus expression products were used to define the optimal dose of IL-12 ARP for use with protein vaccines (see FIGS. 5 and 6); it is believed that recombinant protein preparations purchased for use in experiments described herein contained conventional adjuvanting compounds). Similarly, the licensed, split-product ("TIV") influenza vaccines were used to define the optimal immunization regimens required to achieve the same adjuvant effects with these commercially available vaccines. Various ratios of IL-12 vector and influenza vaccine and the overall dose-sparing effect relative to vaccine alone after one or two immunizations were studied for the generation of humoral (FIGS. 11-12) and cellular (FIGS. 13-14) immune responses. In dose-response studies, the relative adjuvant effect of replicon-vectored IL-12 and soluble, preformed IL-12 cytokine was determined. In these studies, the serum levels of IL-12 in both groups of mice were monitored to demonstrate that the vectored IL-12 approach is effective with much lower systemic levels of IL-12, since its production and adjuvant effect would be limited to the nodes draining the inoculation site. Antibody responses (ELISA) as well as cellular responses (IFNγ ELISPOT) after immunizations were also monitored.

VRPs expressing murine Interleukin-12 (mIL-12) functioned as highly potent adjuvant to co-administered HA protein from type A influenza viruses of H3 and H1 serotypes as well as other protein antigens including a tumor-associated antigen. Preclinical mouse studies were conducted to determine the optimal amounts of IL-12 VRP, and influenza antigens (TIV prepared from inactivated influenza strains) to be included in the VRP adjuvants. In FIG. 12, as an example, at least a 1000-fold dose-sparing effect was observed using $1\times10^6$ IU of IL-12 VRP in combination with TIV (compare bar no. 4 with bar no. 5).

The dose sparing activity of the IL-12 VRP was tested in combination with inactivated vaccines for seasonal influenza. The results are presented in FIGS. 11-14. Mice received one or two immunizations at four week intervals, and humoral immune responses were monitored after each immunization. Cellular T cell responses were measured by ELISPOT at 7 days post-priming immunization in mice with the amounts of TIV and IL12 VRP as described in FIGS. 11 and 12, above. At 1 week post-priming, mice were sacrificed, and splenocytes were analyzed for their frequency of interferon gamma SFC in response to an overlapping peptide libraries generated to correspond to the amino acid sequences of Wyoming HA (FIG. 13) and Wyoming Neuraminidase (NA, FIG. 14). The addition of IL-12 VRP significantly enhances the adaptive immune responses to the components of the TIV. TIV alone failed to induce any detectable T cell responses even at the highest dose of 1000 ng, while the lowest dose tested elicited responses when mixed with IL-12 VRP.

The studies presented in FIGS. 11-14 demonstrated the dose-sparing effects on killed or subunit-based vaccines to elicit functional, protective immune responses against seasonal (H1 and/or H3) as well as potentially pandemic (H5) Influenza virus.

Generation of Alphavirus Replicon Constructs Containing the p35 and p40 Subunits of Murine IL-12, as a Linked Single Open Reading Frame A single-chain murine IL-12 gene, containing the both the p40 and p35 subunits of IL-12, PCR was amplified from the pORF-mIL-12 (p40-35) plasmid (Invivogen) and cloned into IRES and non-IRES replicons.

TABLE 7

Oligonucleotides useful as primers.

| Primer name | Primer sequence | Utility |
|---|---|---|
| mouseIL12ecorv for | CG<u>GATATC</u>ATGGCCTGTCCTCAGAAGC (SEQ ID NO: 1) | These primers were used to PCR amplify |
| mouseIL12rev | CG<u>GGCGCGCC</u>TTAGGCGGAGCTCAGATAG (SEQ ID NO: 2) | and clone mIL-12 into two non-IRES |

TABLE 7-continued

Oligonucleotides useful as primers.

| Primer name | Primer sequence | Utility |
|---|---|---|
| | | containing replicons, pERK and pERK-3 using the EcoRV and AscI restriction sites. To generate IRES replicons containing |
| mil12bamfor | TC<u>GGATCC</u>ATGGCCTGTCCTCAGAAGC (SEQ ID NO: 3) | mIL-12replicons, the gene was initially amplified with these |
| mil12bamrev | CC<u>GGATCC</u>TTAGGCGGAGCTCAGATAGC (SEQ ID NO: 4) | primers and cloned into an IRES containing transfer vector pcDNA3.3/EV71-MS using BamHI sites. The resulting construct was then digested with AscI to release the MS IRES/IL-12 segment which was then cloned into six different PeRK plasmids containing different length stuffers: 257, 342, 357, 383, 579 and 749. |

Restriction sites are underlined

Murine Single Chain IL-12 Coding Sequence from Invivoqen (SEQ ID NO:5)

```
atggcctgtcctcagaagctaaccatctcctggtttgccatcgttttgct
ggtgtctccactcatggccatgtgggagctggagaaagacgtttatgttg
tagaggtggactggactcccgatgcccctggagaaacagtgaacctcacc
tgtgacacgcctgaagaagatgacatcacctggacctcagaccagagaca
tggagtcataggctctggaaagaccctgaccatcactgtcaaagagtttc
tagatgctggccagtacacctgccacaaaggaggcgagactctgagccac
tcacatctgctgctccacaagaaggaaaatggaatttggtccactgaaat
tttaaaaaatttcaaaaacaaagactttcctgaagtgtgaacaccaaatt
actccggacggttcacgtgctcatggctggtgcaaagaaacatggacttg
aagttcaacatcaagagcagtagcagtcccccgactctcgggcagtgac
atgtggaatggcgtctctgtctgcagagaaggtcacactggaccaaaggg
actatgagaagtattcagtgtcctgccaggaggatgtcacctgcccaact
gccgaggagaccctgcccattgaactggcgttggaagcacggcagcagaa
taaatatgagaactacagcaccagcttcttcatcagggacatcatcaaac
cagacccgcccaagaacttgcagatgaagcctttgaagaactcacaggtg
gaggtcagctgggagtaccctgactcctggagcactccccattcctactt
ctccctcaagttctttgttcgaatccagcgcaagaaagaaaagatgaagg
agacagaggaggggtgtaaccagaaaggtgcgttcctcgtagagaagaca
tctaccgaagtccaatgcaaaggcgggaatgtctgcgtgcaagctcagga
tcgctattacaattcctcatgcagcaagtgggcatgtgttccctgcagag
tccgatcggttcctggagtaggggtacctggagtgggcagggtcataccg
gtctctggacctgccaggtgtcttagccagtcccgaaacctgctgaagac
```

-continued

```
cacagatgacatggtgaagacggccagagaaaagctgaaacattattcct
gcactgctgaagacatcgatcatgaagacatcacacgggaccaaaaccag
cacattgaagacctgtttaccactggaactacacaagaacgagagttgcc
tggctactagagagacttcttccacaacaagagggagctgcctgccccca
cagaagacgtctttgatgatgaccctgtgccttggtagcatctatgagga
cttgaagatgtaccagacagagttccaggccatcaacgcagcacttcaga
atcacaaccatcagcagatcattctagacaagggcatgctggtggccatc
gatgagctgatgcagtctctgaatcataatggcgagactctgcgccagaa
acctcctgtgggagaagcagacccttacagagtgaaaatgaagctctgca
tcctgcttcacgccttcagcaccgcgtcgtgaccatcaacagggtgatg
ggctatctgagctccgcctaa
```

The following discussion and definitions are provided to improve the clarity of the present disclosure to one of ordinary skill in the relevant art.

In the context of the present application, nm means nanometer, mL means milliliter, VEE means Venezuelan Equine Encephalitis Virus, EMC means Encephalomyocarditis Virus, BHK means baby hamster kidney cells, HA means hemagglutinin gene, GFP means green fluorescent protein gene, N means nucleocapsid, FACS means fluorescence activated cell sorter, IRES means internal ribosome entry site, pfu means plaque forming units, iu means infectious units, and FBS means Fetal Bovine Serum. The expression "E2 amino acid (e.g., Lys, Thr, etc.) number" indicates designated amino acid at the designated residue of the E2 protein, and is also used to refer to amino acids at specific residues in the E3 or E1 proteins.

As used herein, the term "alphavirus" has its conventional meaning in the art, and includes the various species such as VEE Virus, Semliki Forest Virus (SFV), Sindbis, Ross River Virus, Western Equine Encephalitis Virus, Eastern Equine Encephalitis Virus, Chikungunya Virus, S.A. AR86, Everglades Virus, Mucambo Virus, Barmah Forest Virus, Middleburg Virus, Pixuna Virus, O'nyong-nyong Virus, Getah Virus, Sagiyama Virus, Bebaru Virus, Mayaro Virus, Una Virus, Aura Virus, Whataroa Virus, Banbanki Virus, Kyzylagach Virus, Highlands J Virus, Fort Morgan Virus, Ndumu Virus, and Buggy Creek Virus. Alphaviruses useful in the constructs and methods described herein are VEE, S.A. AR86, Sindbis (e.g. TR339, see U.S. Pat. No. 6,008,035), and SFV.

The terms "5' alphavirus replication recognition sequence" and "3' alphavirus replication recognition sequence" refer to the sequences found in alphaviruses, or sequences derived therefrom, that are recognized by the nonstructural alphavirus replicase proteins and lead to replication of viral RNA. These are sometimes referred to as the 5' and 3' ends, or alphavirus 5' and 3' sequences. The use of these 5' and 3' ends results in replication of the RNA sequence encoded between the two ends. The 3' alphavirus replication recognition sequence as found in the alphavirus is typically approximately 300 nucleotides in length, which contains a more well defined, minimal 3' replication recognition sequence. The minimal 3' replication recognition sequence, conserved among alphaviruses, is a 19 nucleotide sequence (Hill et al., J. Virology, 2693-2704, 1997). These sequences can be modified by standard molecular biological techniques to further minimize the potential for recombination or to introduce cloning sites, with the proviso that they must be recognized by the alphavirus replication machinery.

The term "minimal 5' alphavirus replication recognition sequence" refers to the minimal sequence that allows recognition by the nonstructural proteins of the alphavirus but does not result in significant packaging/recombination of RNA molecules containing the sequence. In a preferred embodiment, the minimal 5' alphavirus replication recognition sequence results in a fifty to one-hundred fold decrease in the observed frequency of packaging/recombination of the RNA containing that sequence. Packaging/recombination of helpers can be assessed by several methods, e.g. the method described by Lu and Silver (J. Virol. Methods 2001, 91(1): 59-65).

The terms "alphavirus RNA replicon", "alphavirus replicon RNA", "alphavirus RNA vector replicon", and "vector replicon RNA" are used interchangeably to refer to an RNA molecule expressing nonstructural protein genes such that it can direct its own replication (amplification) and comprises, at a minimum, 5' and 3' alphavirus replication recognition sequences (which may be the minimal sequences, as defined above, but may alternatively be the entire regions from the alphavirus), coding sequences for alphavirus nonstructural proteins, and a polyadenylation tract. It may additionally contain one or more elements to direct the expression, meaning transcription and translation, of a heterologous RNA sequence. It may also be engineered to express alphavirus structural proteins. Johnston et al., Polo et al. (as cited in the background), Smith et al (International Patent Publication WO 2004/085660) and Smith et al. (U.S. Pat. No. 7,045,335) describe numerous constructs for such alphavirus RNA replicons, and such constructs are incorporated herein by reference. Specific embodiments of the alphavirus RNA replicons may contain one or more attenuating mutations, an attenuating mutation being a nucleotide deletion, addition, or substitution of one or more nucleotide(s), or a mutation that comprises rearrangement or chimeric construction which results in a loss of virulence in a live virus containing the mutation as compared to the appropriate wild-type alphavirus. Examples of an attenuating nucleotide substitution (resulting in an amino acid change in the replicon) include a mutation at nsP1 amino acid position 538, nsP2 amino acid position 96, or nsP2 amino acid position 372 in the alphavirus S.A.AR86, and an example of an attenuating mutation in the non-coding region of the replicon nucleic acid is the substitution of A or C at nucleotide 3 in VEE.

The terms "alphavirus structural protein/protein(s)" refers to one or a combination of the structural proteins encoded by alphaviruses. These are produced by the virus as a polyprotein and are represented generally in the literature as C-E3-E2-6k-E1. E3 and 6k serve as membrane translocation/transport signals for the two glycoproteins, E2 and E1. Thus, use of the term E1 herein can refer to E1, E3-E1, 6k-E1, or E3-6k-E1, and use of the term E2 herein can refer to E2, E3-E2, 6k-E2, or E3-6k-E2. Attenuating mutations can be introduced into any one or more of the alphavirus structural proteins.

The term "helper(s)" or "helper construct(s)", refer to a nucleic acid molecule that is capable of expressing one or more alphavirus structural proteins. Johnston et al., Polo et al. (as cited in the background), Smith et al (International Patent Publication WO 2004/085660) and Smith et al. (U.S. Pat. No. 7,045,335) describe numerous helper constructs useful for expressing alphavirus structural proteins in the production of ARPs.

The terms "helper cell" and "packaging cell" are used interchangeably herein and refer to the cell in which alphavirus replicon particles are produced. The helper cell comprises a set of helpers that encode one or more alphavirus structural proteins. As disclosed herein, the helpers may be RNA or DNA. The cell can be any cell that is alphavirus-permissive, i.e. cells that are capable of producing alphavirus particles upon introduction of a viral RNA transcript. Alphavirus-permissive cells include, but are not limited to, Vero, baby hamster kidney (BHK), 293, 293T, chicken embryo fibroblast (CEF), and Chinese hamster ovary (CHO) cells. In certain embodiments, the helper or packaging cell may additionally include a heterologous RNA-dependent RNA polymerase and/or a sequence-specific protease. The nucleic acids encoding alphavirus structural proteins can be present in the helper cell transiently or by stable integration into the genome of the helper cell. The nucleic acid encoding the alphavirus structural proteins that are used to produce alphavirus particles can be under the control of constitutive and/or inducible promoters. In one embodiment, the alpha virus structural protein coding sequences can be provided on a single DNA helper (see Smith et al U.S. Pat. No. 7,045,335) or as two helper constructs comprising an IRES element in which the translation of these coding sequences can be controlled by the activity of an IRES element. In such embodiments, the IRES element can be active in the specific helper cell type and not active, or minimally active in other cells types. In particular embodiments, the helper cells comprise nucleic acid sequences encoding the alphavirus structural proteins in a combination and/or amount sufficient to produce an alphavirus particle when a recombinant replicon nucleic acid is introduced into the cell under conditions whereby the alphavirus structural proteins are produced and the recombinant replicon nucleic acid is packaged into alphavirus particles disclosed herein.

The terms "alphavirus replicon particles", "virus replicon particles" or "recombinant alphavirus particles", used interchangeably herein, mean a virion-like structural complex incorporating an alphavirus replicon RNA that expresses one or more heterologous RNA sequences. Typically, the virion-like structural complex includes one or more alphavirus structural proteins embedded in a lipid envelope enclosing a nucleocapsid that in turn encloses the RNA. The lipid envelope is typically derived from the plasma membrane of the cell in which the particles are produced. Preferably, the alphavirus replicon RNA is surrounded by a nucleocapsid structure comprised of the alphavirus capsid protein, and the alphavirus glycoproteins are embedded in the cell-derived lipid envelope. The structural proteins and replicon RNA may be derived from the same or different alphaviruses. In a specific embodiment, the replicon RNA and structural proteins are from VEE, e.g. see Smith et al., U.S. Patent Publication 2005-0266550. In another embodiment, the replicon RNA is derived from VEE and the structural proteins are derived from Sindbis Virus (see, e.g. Dubensky et al., U.S. Pat. No. 6,376, 236). The alphavirus replicon particles are infectious but propagation-defective, i.e. the replicon RNA cannot propagate beyond the host cell into which the particles initially infect, in the absence of the helper nucleic acid(s) encoding the alphavirus structural proteins.

A promoter for directing transcription of RNA from DNA, i.e. a DNA dependent RNA polymerase, is employed to produce the alphavirus replicon and helper nucleic acids provided herein. In the present context, a promoter is a sequence of nucleotides recognized by a polymerase and sufficient to cause transcription of an associated (downstream) sequence. In some embodiments, the promoter is constitutive (see below). Alternatively, the promoter may be regulated, i.e., not constitutively acting to cause transcription of the associated sequence. If inducible, there are sequences present which mediate regulation of expression so that the associated sequence is transcribed only when (i) an inducer molecule is present in the medium in or on which the cells are cultivated, or (ii) conditions to which the cells are exposed are changed to be inducing conditions. In the present context, a transcription regulatory sequence includes a promoter sequence and can further include cis-active sequences for regulated expression of an associated sequence in response to environmental signals.

In certain embodiments of replicon and helper RNAs, transcription and translation are controlled separately by different regulatory elements. The replicon contains a promoter that directs transcription; an IRES element; and a coding sequence (e.g. for a heterologous protein or fragment), in which the IRES element is operably located such that translation of the coding sequence is via a cap-independent mechanism directed by the IRES element and not via a cap-dependent mechanism. The term "transcription" as used herein includes the production of RNA from an alphavirus subgenomic promoter of a recombinant replicon nucleic acid, which can itself be an RNA molecule. That is, the subgenomic promoter on a recombinant replicon or helper RNA molecule can direct the transcription of a messenger RNA encoding a heterologous nucleic acid of interest or an alphavirus structural protein. Separately, the recombinant replicon or helper nucleic acid can be "replicated," i.e., copied from the 5' replication recognition sequence through to the replication recognition sequence.

In RNA helper embodiments and to produce the replicon RNA, a promoter is utilized to synthesize RNA in an in vitro transcription reaction, and specific promoters suitable for this use include the SP6, T7, and T3 RNA polymerase promoters. In the DNA helper embodiments, the promoter functions within a cell to direct transcription of RNA. Potential promoters for in vivo transcription of the construct include eukaryotic promoters such as RNA polymerase II promoters, RNA polymerase III promoters, or viral promoters such as MMTV and MoSV LTR, SV40 early region, RSV or CMV. Many other suitable mammalian and viral promoters are available in the art. Alternatively, DNA dependent RNA polymerase promoters from bacteria or bacteriophage, e.g. SP6, T7, and T3, may be employed for use in vivo, with the matching RNA polymerase being provided to the cell, either via a separate plasmid, RNA vector, or viral vector. In a specific embodiment, the matching RNA polymerase can be stably transformed into a helper cell line under the control of an inducible promoter.

In certain constructs, control of nucleic acid expression at the level of translation is accomplished by introducing an internal ribosome entry site (IRES) downstream of the promoter, e.g. the alphavirus 26S subgenomic promoter, and upstream of the coding sequence, e.g. for the heterologous sequence or an alphavirus structural protein, to be translated. The IRES element is positioned so that it directs translation of the mRNA, thereby minimizing, limiting or preventing initiation of translation of the mRNA from the methyl-7-guanosine (5')pppN structure present at the 5' end of the subgenomic mRNA (the "cap"). These constructs result in the IRES controlling translation of a heterologous sequence independently of promoter-driven transcription. IRESes from many different sources can be employed, including viral IRES elements from picornaviruses, e.g., poliovirus (PV) or the human enterovirus 71, e.g. strains 7423/MS/87 and BrCr thereof; from encephalomyocarditis virus (EMCV); from foot-and-mouth disease virus (FMDV); from flaviviruses, e.g., hepatitis C virus (HCV); from pestiviruses, e.g., classical swine fever virus (CSFV); from retroviruses, e.g., murine leukemia virus (MLV); from lentiviruses, e.g., simian immunodeficiency virus (Sly); from cellular mRNA IRES elements such as those from translation initiation factors, e.g., eIF4G or DAP5; from transcription factors, e.g., c-Myc or NF-κB-repressing factor (NRF); from growth factors, e.g., vascular endothelial growth factor (VEGF), fibroblast growth factor (FGF-2) and platelet-derived growth factor B (PDGF B); from homeotic genes, e.g., Antennapedia; from survival proteins, e.g., X-linked inhibitor of apoptosis (XIAP) or Apaf-1; from chaperones, e.g., immunoglobulin heavy-chain binding protein BiP, plant viruses, as well as any other IRES elements now known or later.

The IL-12 expressing ARP preparations are used as an adjuvant with other immunogenic preparations. Such immunogenic preparations can include an antigen, an immunogen or immunogenic polypeptide or peptide, a fusion protein, a fusion peptide, a cancer or tumor antigen, an aberrant polypeptide responsible for a disease, e.g. Alzheimers. Examples of such immunogenic polypeptides and peptides are suitable for protecting a subject against a disease, including but not limited to microbial, bacterial, protozoal, parasitic, and viral diseases. These immunogenic preparations can be in the form of purified protein or protein fragments extracted from the source (i.e. the virus, prokaryote or eukaryote); DNA capable of expressing such immunogenic molecules; inactivated virus preparations such as TIV, and viral or bacterial vectors expressing such immunogenic molecules.

Any amino acids which occur in the amino acid sequences referred to in the specification have their usual three- and one-letter abbreviations routinely used in the art: A, Ala, Alanine; C, Cys, Cysteine; D, Asp, Aspartic Acid; E, Glu, Glutamic Acid; F, Phe, Phenylalanine; G, Gly, Glycine; H, His, Histidine; I, Ile, Isoleucine; K, Lys, Lysine; L, Leu, Leucine; M, Met, Methionine; N, Asn, Asparagine; P, Pro, Proline; Q, Gln, Glutamine; R, Arg, Arginine; S, Ser, Serine; T, Thr, Threonine; V, Val, Valine; W, Try, Tryptophan; Y, Tyr, Tyrosine.

As used herein, expression directed by a particular sequence is the transcription of an associated downstream sequence. If appropriate and desired for the associated sequence, there the term expression also encompasses translation (protein synthesis) of the transcribed or introduced RNA. Alternatively, different sequences can be used to direct transcription and translation.

Alphavirus-permissive cells employed in the present methods are cells that, upon transfection with a complete viral RNA transcript, are capable of producing viral particles. Alphaviruses have a broad host range. Examples of suitable packaging cells include, but are not limited to, Vero cells, baby hamster kidney (BHK) cells, chicken embryo fibroblast cells, DF-1, 293, 293T, Chinese Hamster Ovary (CHO) cells, and insect cells.

The phrases "structural protein" or "alphavirus structural protein" as used herein refer to one or more of the alphaviral-encoded proteins which are required for packaging of the RNA replicon, and typically include the capsid protein, E1 glycoprotein, and E2 glycoprotein in the mature alphavirus (certain alphaviruses, such as Semliki Forest Virus, contain an additional protein, E3, in the mature coat). The term "alphavirus structural protein(s)" refers to one or a combination of the structural proteins encoded by alphaviruses. These are synthesized (from the viral genome) as a polyprotein and are represented generally in the literature as C-E3-E2-6k-E1. E3 and 6k serve as membrane translocation/transport signals for the two glycoproteins, E2 and E1. Thus, use of the term E1 herein can refer to E1, E3-E1, 6k-E1, or E3-6k-E1, and use of the term E2 herein can refer to E2, E3-E2, 6k-E2, or E3-6k-E2.

The structural proteins of the alphavirus are distributed among one or more helper nucleic acid molecules (e.g., a first helper RNA (or DNA) and a second helper RNA (or DNA). In addition, one or more structural proteins may be located on the same molecule as the replicon nucleic acid, provided that at least one structural protein is deleted from the replicon RNA such that the replicon and resulting alphavirus particle are replication defective. As used herein, the terms "deleted" or "deletion" mean either total deletion of the specified segment or the deletion of a sufficient portion of the specified segment to render the segment inoperative or nonfunctional, in accordance with standard usage. See, e.g., U.S. Pat. No. 4,650,764 to Temin et al. The term "replication defective" as used herein is synonymous with "propagation-defective", and means that the particles produced in a given host cell cannot produce progeny particles in the host cell, due to the absence of the helper function, i.e. the alphavirus structural proteins required for packaging the replicon nucleic acid. However, the replicon nucleic acid is capable of replicating itself and being expressed within the host cell into which it has been introduced.

Methods for the economical and efficient production of high yield particles are described in U.S. Pat. No. 7,078,218, issued Jul. 18, 2006, as are specific attenuated strains and viruses useful for the expression of an expressible IL-12 coding sequence.

The helper cell, also referred to as a packaging cell, used to produce the infectious, replication defective alphavirus particles, must express or be capable of expressing alphavirus structural proteins sufficient to package the replicon nucleic acid. The structural proteins can be produced from a set of RNAs, typically two that are introduced into the helper cell concomitantly with or prior to introduction of the replicon vector. The first helper RNA includes RNA encoding at least one alphavirus structural protein but does not encode all alphavirus structural proteins. The first helper RNA may comprise RNA encoding the alphavirus E1 glycoprotein, but not encoding the alphavirus capsid protein and the alphavirus E2 glycoprotein. Alternatively, the first helper RNA may comprise RNA encoding the alphavirus E2 glycoprotein, but not encoding the alphavirus capsid protein and the alphavirus E1 glycoprotein. In a further embodiment, the first helper RNA may comprise RNA encoding the alphavirus E1 glycoprotein and the alphavirus E2 glycoprotein, but not the alphavirus capsid protein. In a fourth embodiment, the first helper RNA may comprise RNA encoding the alphavirus capsid, but none of the alphavirus glycoproteins. In a fifth embodiment, the first helper RNA may comprise RNA encoding the capsid and one of the glycoproteins, i.e. either E1 or E2, but not both.

In combination with any one of these first helper RNAs, the second helper RNA encodes at least one alphavirus structural protein not encoded by the first helper RNA. For example, where the first helper RNA encodes only the alphavirus E1 glycoprotein, the second helper RNA may encode one or both of the alphavirus capsid protein and the alphavirus E2 glycoprotein. Where the first helper RNA encodes only the alphavirus capsid protein, the second helper RNA may include RNA encoding one or both of the alphavirus glycoproteins. Where the first helper RNA encodes only the alphavirus E2 glycoprotein, the second helper RNA may encode one or both of the alphavirus capsid protein and the alphavirus E1 glycoprotein. Where the first helper RNA encodes both the capsid and alphavirus E1 glycoprotein, the second helper RNA may include RNA encoding one or both of the alphavirus capsid protein and the alphavirus E2 glycoprotein.

In the helper nucleic acids, it is understood that these molecules further comprise sequences necessary for expression (encompassing translation and where appropriate, transcription or replication signals) of the encoded structural protein sequences in the helper cells. Such sequences can include, for example, promoters, (either viral, prokaryotic or eukaryotic, inducible or constitutive), IRES elements, and 5' and 3' viral replicase recognition sequences. In the case of the helper nucleic acids expressing one or more glycoproteins, it is understood from the art that these sequences are advantageously expressed with a leader or signal sequence at the N-terminus of the structural protein coding region in the nucleic acid constructs. The leader or signal sequence can be derived from the alphavirus, for example E3 or 6k, or it can be a heterologous sequence such as a tissue plasminogen activator signal peptide or a synthetic sequence. Thus, as an example, a first helper nucleic acid may be an RNA molecule encoding capsid-E3-E1, and the second helper nucleic acid may be an RNA molecule encoding capsid-E3-E2. Alternatively, the first helper RNA can encode capsid alone, and the second helper RNA can encode E3-E2-6k-E1. Additionally, the packaging signal or "encapsidation sequence" that is present in the viral genome is not present in all of the helper nucleic acids. Preferably, the packaging signal is deleted from all of the helper nucleic acids.

These RNA helpers can be introduced into the cells in a number of ways. They can be expressed from one or more expression cassettes that have been stably transformed into the cells, thereby establishing packaging cell lines (see, for example, U.S. Pat. No. 6,242,259). Alternatively, the RNAs can be introduced as RNA or DNA molecules that can be expressed in the helper cell without integrating into the cell genome. Methods of introduction include electroporation, viral vectors (e.g. SV40, adenovirus, nodavirus, astrovirus), and lipid-mediated transfection.

An alternative to multiple helper RNAs is the use of a single DNA molecule, which encodes all the polypeptides necessary for packaging the viral replicon RNA into infective alphavirus replicon particles. The single DNA helper can be introduced into the packaging cell by any means known to the art, including but not limited to electroporation, lipid-mediated transfection (lipofection), viral vectored (e.g. adenovirus or SV-40), or calcium phosphate-mediated transfection. Preferably, the DNA is introduced via the electroporation-based methods. The DNA is typically electroporated into cells with a decrease in voltage and an increase in capacitance, as compared to that required for the uptake of RNA. In all electroporations, the value for the voltage and capacitance must be set so as to avoid destroying the ability of the packaging (host) cells to produce infective alphavirus particles. Alternatively, the helper function, in this format and under an inducible promoter, can be incorporated into the packaging cell genome prior to the introduction/expression of the RNA vector replicon, and then induced with the appropriate stimulus just prior to, concomitant with, or after the introduction of the RNA vector replicon.

Advantageously, one or more of the nucleic acids encoding the alphavirus structural proteins, i.e., the capsid, E1 glycoprotein and E2 glycoprotein, or the replicon construct, contains one or more attenuating mutations. The phrases "attenuating mutation" and "attenuating amino acid," as used herein, mean a nucleotide mutation (which may or may not be in a region of the viral genome encoding polypeptides) or an amino acid coded for by a nucleotide mutation, which in the context of a live virus, result in a decreased probability of the alphavirus causing disease in its host (i.e., a loss of virulence), in accordance with standard terminology in the art, See, e.g., B. Davis, et al., Microbiology 156-158, (4th ed. 1990), whether the mutation be a substitution mutation, or an in-frame deletion or addition mutation. The phrase "attenuating mutation" excludes mutations which would be lethal to the virus, unless such a mutation is used in combination with a "restoring" mutation which renders the virus viable, albeit attenuated. Methods for identifying suitable attenuating mutations in the alphavirus genome are known in the art. Olmsted et al. (1984; Science 225:424) describes a method of identifying attenuating mutations in Sindbis virus by selecting for rapid growth in cell culture. Johnston and Smith (1988; Virology 162:437) describe the identification of attenuating mutations in VEE by applying direct selective pressure for accelerated penetration of BHK cells. Attenuating mutations in alphaviruses have been described in the art, e.g. White et al. 2001 *J. Virology* 75:3706; Kinney et al. 1989 *Virology* 70:19; Heise et al. 2000 *J. Virology* 74:4207; Bernard et al 2000 *Virology* 276:93; Smith et al 2001 *J. Virology* 75:11196; Heidner and Johnston 1994 *J. Virology* 68:8064; Klimstra et al. 1999 *J. Virology* 73:10387; Glasgow et al. 1991 *Virology* 185:741; Polo and Johnston 1990 *J. Virology* 64:4438; and Smerdou and Liljestrom 1999 *J. Virology* 73:1092.

In certain embodiments, the replicon RNA comprises at least one attenuating mutation. In other specific embodiments, the helper nucleic acid(s) include at least one attenuating mutation. In embodiments comprising two helper nucleic acid molecules, at least one molecule includes at least one attenuating mutation, or both can encode at least one attenuating mutation. Alternatively, the helper nucleic acid, or at least one of the first or second helper nucleic acids includes at least two, or multiple, attenuating mutations. Appropriate attenuating mutations depend upon the alphavirus used. For example, when the alphavirus is VEE, suitable attenuating mutations may be selected from the group consisting of codons at E2 amino acid position 76 which specify an attenuating amino acid, preferably lysine, arginine, or histidine as E2 amino acid 76; codons at E2 amino acid position 120 which specify an attenuating amino acid, preferably lysine as E2 amino acid 120; codons at E2 amino acid position 209 which specify an attenuating amino acid, preferably lysine, arginine, or histidine as E2 amino acid 209; codons at E1 amino acid 272 which specify an attenuating mutation, preferably threonine or serine as E1 amino acid 272; codons at E1 amino acid 81 which specify an attenuating mutation, preferably isoleucine or leucine as E1 amino acid 81; and codons at E1 amino acid 253 which specify an attenuating mutation, preferably serine or threonine as E1 amino acid 253. Additional attenuating mutations include deletions or substitution mutations in the cleavage domain between E3 and E2 such that the E3/E2 polyprotein is not cleaved; this mutation in combination with the mutation at E1-253 can be used in the present methods and compositions. Similarly, mutations present in existing live vaccine strains, e.g. strain TC83 (see Kinney et al., 1989, Virology 170: 19-30, particularly the mutation at nucleotide 3), can be used.

Where the alphavirus is the South African Arbovirus No. 86 (S.A. AR86), suitable attenuating mutations may be selected from the group consisting of codons at nsP1 amino acid position 538 which specify an attenuating amino acid, preferably isoleucine as nsP1 amino acid 538; codons at E2 amino acid position 304 which specify an attenuating amino acid, preferably threonine as E2 amino acid position 304; codons at E2 amino acid position 314 which specify an attenuating amino acid, preferably lysine as E2 amino acid 314; codons at E2 amino acid position 376 which specify an attenuating amino acid, preferably alanine as E2 amino acid 376; codons at E2 amino acid position 372 which specify an attenuating amino acid, preferably leucine as E2 amino acid 372; codons at nsP2 amino acid position 96 which specify an attenuating amino acid, preferably glycine as nsP2 amino acid 96; and codons at nsP2 amino acid position 372 which specify an attenuating amino acid, preferably valine as nsP2 amino acid 372. Suitable attenuating mutations useful in embodiments wherein other alphaviruses are employed are known to those skilled in the art.

Attenuating mutations may be introduced into the RNA by performing site-directed mutagenesis on the cDNA which encodes the RNA, in accordance with known procedures. See, Kunkel, *Proc. Natl. Acad. Sci. USA* 82:488 (1985), the disclosure of which is incorporated herein by reference in its entirety. Alternatively, mutations may be introduced into the RNA by replacement of homologous restriction fragments in the cDNA which codes for the RNA, in accordance with known procedures, or in cDNA copies using mutagenic polymerase chain reaction methods.

In alphavirus replicon particles (ARPs), an alphavirus vector, herein referred to as a replicon, is engineered to contain and express one or more genes of interest, where the gene of interest can encode, IL-12, or in the case of the antigen preparation being adjuvanted by IL-12 expressing VRP, the antigen. The alphavirus replicon vector can be derived from any alphavirus, such as Venezuelan Equine Encephalitis (VEE) virus, Sindbis virus, e.g. strain TR339, South African Arbovirus No. 86, and Semliki Forest virus, among others. The vector is then introduced into cells in culture that allow replication of alphaviruses and in which the structural proteins of the alphavirus are also expressed, so that the vector is packaged by the structural proteins into ARPs which are eventually released from the cell. Methods for the preparation of infective, propagation-defective, adjuvant alphavirus replicon particles in high yields are described in U.S. Pat. No. 7,018,218.

As used herein, interleukin-12 is a protein known to the art. This cytokine is functional in the form of a heterodimer consisting of a p35 and a p40 subunit. IL-12 is known to augment IFN-gamma secretion and cytolytic activity of natural killer cells and cytotoxic T-lymphoctyes, and it plays a key role in the generation of the T-helper type 1 immune response. Desirably, the sequence of an IL-12 used in the IL-12 expressing ARPs has an amino acid sequence substantially the same as that of the species into which the IL-12 ARP adjuvanted immunogenic composition is administered.

It is recognized by those skilled in the art that the coding sequences may vary due to the degeneracy of the genetic code and codon usage. All synonymous sequences which code for the antigen or other polypeptide or protein of interest are included within the scope of this application.

Additionally, it is recognized by those skilled in the art that allelic variations may occur in the coding sequences which do not significantly change activity of the amino acid sequences of the peptides which those sequences encode. All such equivalent DNA sequences are included within the scope of this application.

Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al. (1989) *Molecular Cloning*, Second Edition, Cold Spring Harbor Laboratory, Plainview, N.Y.; Maniatis et al. (1982) *Molecular Cloning*, Cold Spring Harbor Laboratory, Plainview, N.Y.; Wu (ed.) (1993) *Meth. Enzymol.* 218, Part I; Wu (ed.) (1979) *Meth. Enzymol.* 68; Wu et al. (eds.) (1983) *Meth. Enzymol.* 100 and 101; Grossman and Moldave (eds.) *Meth. Enzymol.* 65; Miller (ed.) (1972) *Experiments in Molecular Genetics*, Cold Spring Harbor Laboratory, Cold Spring Harbor, N.Y.; Old and Primrose (1981) *Principles of Gene Manipulation*, University of California Press, Berkeley; Schleif and Wensink (1982) *Practical Methods in Molecular Biology*; Glover (ed.) (1985) *DNA Cloning* Vol. I and II, IRL Press, Oxford, UK; Hames and Higgins (eds.) (1985) *Nucleic Acid Hybridization*, IRL Press, Oxford, UK; Setlow and Hollaender (1979) *Genetic Engineering: Principles and Methods*, Vols. 1-4, Plenum Press, New York; and Ausubel et al. (1992) *Current Protocols in Molecular Biology*, Greene/Wiley, New York, N.Y. Abbreviations and nomenclature, where employed, are deemed standard in the field and commonly used in professional journals such as those cited herein.

Pharmaceutical formulations, such as vaccines or other immunogenic compositions, as provided herein, comprise an immunogenic amount of the infectious, propagation defective alphavirus replicon particles or live, attenuated particles in combination with a pharmaceutically acceptable carrier. An "immunogenic amount" is an amount of the infectious alphavirus particles which is sufficient to evoke an immune response in the subject to which the pharmaceutical formulation is administered. An amount of from about $10^4$ to about $10^9$, especially $10^6$ to $10^8$, infectious units, or ARPs per dose is believed suitable, depending upon the age and species of the subject being treated. Exemplary pharmaceutically acceptable carriers include, but are not limited to, sterile pyrogen-free water and sterile pyrogen-free physiological saline solution. Subjects which may be administered immunogenic amounts of the infectious, replication defective alphavirus particles include human and animal (e.g., dog, cat, cattle, horse, donkey, mouse, hamster, monkeys, guinea pigs, birds, eggs) subjects. Administration may be by any suitable means, such as intraperitoneal, intramuscular, intradermal, intranasal, intravaginal, intrarectal, subcutaneous or intravenous administration.

Immunogenic compositions comprising the ARPs (which direct the expression of the sequence(s) of interest when the compositions are administered to a human or animal) may be formulated by any of the means known in the art. Such compositions, especially vaccines, are typically prepared as injectables, either as liquid solutions or suspensions. Solid forms suitable for solution in, or suspension in, liquid prior to injection may also be prepared. Lyophilized preparations are also suitable.

The active immunogenic ingredients (the ARPs) are often mixed with excipients or carriers which are pharmaceutically acceptable and compatible with the active ingredient. Suitable excipients include but are not limited to sterile water, saline, dextrose, glycerol, ethanol, or the like and combinations thereof, as well as stabilizers, e.g. HSA or other suitable proteins and reducing sugars In addition, if desired, the vaccines may contain minor amounts of auxiliary substances such as wetting or emulsifying agents, pH buffering agents, and/or adjuvants which enhance the effectiveness of the vaccine. Examples of adjuvants which may be effective include but are not limited to: aluminum hydroxide; N-acetyl-muramyl-L-threonyl-D-isoglutamine (thr-MDP); N-acetyl-nor-muramyl-L-alanyl-D-isoglutamine (CGP 11637, referred to as nor-MDP); N-acetylmuramyl-L-alanyl-D-isoglutaminyl-L-alanine-2-(1'-2'-dipalmitoyl-sn-glycero-3hydroxyphosphoryloxy)-ethylamine (CGP 19835A, referred to as MTP-PE); and RIBI, which contains three components extracted from bacteria, monophosphoryl lipid A, trehalose dimycolate and cell wall skeleton (MPL+TDM+CWS) in a 2% squalene/Tween 80 emulsion. The effectiveness of an adjuvant may be determined by measuring the amount of antibodies directed against the immunogenic product of the ARP resulting from administration of the immunogen in vaccines which are also comprised of the various adjuvants. Such additional formulations and modes of administration as are known in the art may also be used.

The immunogenic (or otherwise biologically active) ARP-containing compositions are administered in a manner compatible with the dosage formulation, and in such amount as is prophylactically and/or therapeutically effective. The quantity to be administered, which is generally in the range of about $10^4$ to about $10^9$ infectious units per mL in a dose, depends on the subject to be treated, the route by which the ARPs are administered, the immunogenicity of the expression product, the types of effector immune responses desired, and the degree of protection desired. Precise amounts of the active ingredient required to be administered may depend on the judgment of the physician, veterinarian or other health practitioner and may be peculiar to each individual, but such a determination is within the skill of such a practitioner.

The vaccine or other immunogenic composition may be given in a single dose or multiple dose schedule. A multiple dose schedule is one in which a primary course of vaccination may include 1 to 10 or more separate doses, followed by other doses administered at subsequent time intervals as required to maintain and or reinforce the immune response, e.g., weekly or at 1 to 4 months for a second dose, and if needed, a subsequent dose(s) after several months/years.

All references cited herein are hereby incorporated by reference to the extent there is no inconsistency with the present disclosure. The references cited in the present disclosure reflect the level of skill in the relevant arts.

Although the description herein contains certain specific information and examples, these should not be construed as limiting the scope of the invention as claimed but as merely providing illustrations of some of the possible embodiments of the invention. For example, thus the scope of the invention should be determined by the appended claims and their equivalents, rather than by the examples given, but the invention may be further understood by the non-limiting examples given herein above.

We claim:

1. A method of enhancing an immune response to an antigen administered to a subject comprising administering to the subject a dose of an antigen and further or simultaneously administering alphavirus replicon particles expressing IL-12, wherein the alphavirus replicon particles are Venezuelan equine encephalitis (VEE) virus replicon particles.

2. The method of claim 1, wherein the enhanced immune response is a humoral (antibody) response.

3. The method of claim 2, wherein the immune response is enhanced at least three-fold over the response to the antigen in the absence of alphavirus replicon particles expressing interleukin-12 (IL-12).

4. The method of claim 1, wherein the enhanced immune response is a cellular response.

5. A method of reducing the risk of contracting a disease or reducing the severity of a disease in a subject comprising administering (a) an antigen selected from the microorganism or virus that causes the disease, and (b) alphavirus replicon particles expressing IL-12, wherein the alphavirus replicon particles are Venezuelan equine encephalitis (VEE) virus replicon particles.

6. A vaccine composition comprising (a) an antigen preparation selected from the group consisting of a protein, glycoprotein, lipoprotein, the expression product of a minigene which product comprises a linear string of epitopes of interest, a linear string of epitopes of a virus hemagglutinin, a linear string of epitopes from an influenza virus hemagglutinin, a toxin, attenuated toxin, inactivated toxin, virus, attenuated virus, inactivated virus, bacterial cells or portion(s) thereof, inactivated bacteria, attenuated bacteria, fungal cells or portion(s) thereof, attenuated fungus, inactivated fungus, parasite or portion(s) thereof, inactivated parasite, attenuated parasite, protozoan or portion(s) thereof, inactivated protozoan or portions thereof, attenuated protozoan, DNA capable of expressing an antigen or fragments or epitopes thereof, pox virus vectored immunogen, alphavirus-vectored or an adenovirus-vectored immunogen, tumor cell antigen or tissue or portion thereof, polysaccharide, lipopolysaccharide, lipooligosaccharide or other material capable of eliciting an immune response in a human or animal to which it is administered; and (b) alphavirus replicon particles which express interleukin-12, wherein the alphavirus replicon particles are Venezuelan equine encephalitis (VEE) virus replicon particles.

7. The vaccine composition of claim 6, wherein the antigen preparation is a protein.

8. The vaccine composition of claim 6, wherein the antigen preparation is alphavirus replicon particles which express the protein.

9. A method of immunizing a subject comprising administering a single dose of the vaccine composition of claim 6.

10. The method according to claim 2, wherein the antigen is selected from the group consisting of a protein, glycoprotein, lipoprotein, the expression product of a minigene which product comprises a linear string of epitopes of interest, a linear string of epitopes of a virus hemagglutinin, a linear string of epitopes from an influenza virus hemagglutinin, a toxin, attenuated toxin, inactivated toxin, virus, attenuated virus, inactivated virus, bacterial cells or portion(s) thereof, inactivated bacteria, attenuated bacteria, fungal cells or portion(s) thereof, attenuated fungus, inactivated fungus, parasite or portion(s) thereof, inactivated parasite, attenuated parasite, protozoan or portion(s) thereof, inactivated protozoan or portions thereof, attenuated protozoan, DNA capable of expressing an antigen or fragments or epitopes thereof, pox virus vectored immunogen, alphavirus-vectored or an adenovirus-vectored immunogen, tumor cell antigen or tissue or portion thereof, polysaccharide, lipopolysaccharide, lipooligosaccharide and other material capable of eliciting an immune response in a human or animal to which it is administered.

11. The method according to claim 4, wherein the antigen is selected from the group consisting of a protein, glycoprotein, lipoprotein, the expression product of a minigene which product comprises a linear string of epitopes of interest, a linear string of epitopes of a virus hemagglutinin, a linear string of epitopes from an influenza virus hemagglutinin, a toxin, attenuated toxin, inactivated toxin, virus, attenuated virus, inactivated virus, bacterial cells or portion(s) thereof, inactivated bacteria, attenuated bacteria, fungal cells or portion(s) thereof, attenuated fungus, inactivated fungus, parasite or portion(s) thereof, inactivated parasite, attenuated parasite, protozoan or portion(s) thereof, inactivated protozoan or portions thereof, attenuated protozoan, DNA capable of expressing an antigen or fragments or epitopes thereof, pox virus vectored immunogen, alphavirus-vectored or an adenovirus-vectored immunogen, tumor cell antigen or tissue or portion thereof, polysaccharide, lipopolysaccharide, lipooligosaccharide and other material capable of eliciting an immune response in a human or animal to which it is administered.

12. The method of claim 9, wherein the antigen preparation is a protein.

13. The method of claim 9, wherein the effective dose of the antigen preparation is at least five-fold lower than the dose of the antigen required in the absence of alphavirus replicon particles expressing IL-12 to provide effective immunization against the antigen.

14. The method of claim 1, wherein the immunogen and the alphavirus replicon particles are administered to the subject simultaneously and in a same location.

15. The method of claim 1, wherein the antigen is expressed from a VEE virus replicon particle separate from the IL-12-expressing VEE replicon particles, and the dose of the antigen-expressing VEE virus replicon particles is equal to or greater than the dose of VEE virus replicon particles expressing IL-12.

16. The method of claim 1, wherein a first step comprising administering simultaneously to the subject the antigen and the alphavirus replicon particles expressing IL-12 as a priming administration, is followed by subsequently administering a second dose of the antigen in the absence of the alphavirus replicon particles expressing IL-12.

17. The method of claim 16, wherein the modality of the second dose is selected from the group consisting of protein, inactivated virus, DNA, viral-vectored antigens, and virus-like particles displaying the antigen.

* * * * *

SEQUENCE LISTING

<160> NUMBER OF SEQ ID NOS: 5

<210> SEQ ID NO 1
<211> LENGTH: 27
<212> TYPE: DNA
<213> ORGANISM: Artificial
<220> FEATURE:
<223> OTHER INFORMATION: Synthetic construct: oligonucleotide useful as a primer.

<400> SEQUENCE: 1
cggatatcat ggcctgtcct cagaagc                                              27

<210> SEQ ID NO 2
<211> LENGTH: 29
<212> TYPE: DNA
<213> ORGANISM: Artificial
<220> FEATURE:
<223> OTHER INFORMATION: Synthetic construct: oligonucleotide useful as a primer.

<400> SEQUENCE: 2
cgggcgcgcc ttaggcggag ctcagatag                                            29

<210> SEQ ID NO 3
<211> LENGTH: 27
<212> TYPE: DNA
<213> ORGANISM: Artificial
<220> FEATURE:
<223> OTHER INFORMATION: Synthetic construct: oligonucleotide useful as a primer.

<400> SEQUENCE: 3
tcggatccat ggcctgtcct cagaagc                                              27

<210> SEQ ID NO 4
<211> LENGTH: 28
<212> TYPE: DNA
<213> ORGANISM: Artificial
<220> FEATURE:
<223> OTHER INFORMATION: Synthetic construct: oligonucleotide useful as a primer.

<400> SEQUENCE: 4
ccggatcctt aggcggagct cagatagc                                             28

<210> SEQ ID NO 5
<211> LENGTH: 1620
<212> TYPE: DNA
<213> ORGANISM: Artificial
<220> FEATURE:
<223> OTHER INFORMATION: Synthetic construct: coding sequence of murine interleukin-12.

<400> SEQUENCE: 5
atggcctgtc ctcagaagct aaccatctcc tggtttgcca tcgttttgct ggtgtctcca    60
ctcatggcca tgtgggagct ggagaaagac gtttatgttg tagaggtgga ctggactccc   120
gatgcccctg agaaacagt gaacctcacc tgtgacacgc tgaagaaga tgacatcacc     180 tggacctcag accagagaca tggagtcata ggctctggaa agaccctgac catcactgtc   240
aaagagtttc tagatgctgg ccagtacacc tgccacaaag gaggcgagac tctgagccac   300
tcacatctgc tgctccacaa gaaggaaaat ggaatttggt ccactgaaat ttaaaaaat    360 ttcaaaaaca agactttcct gaagtgtgaa gcaccaaatt actccggacg gttcacgtgc   420

-continued

```
tcatggctgg tgcaaagaaa catggacttg aagttcaaca tcaagagcag tagcagtccc    480
cccgactctc gggcagtgac atgtggaatg gcgtctctgt ctgcagagaa ggtcacactg    540
gaccaaaggg actatgagaa gtattcagtg tcctgccagg aggatgtcac ctgcccaact    600
gccgaggaga ccctgcccat tgaactggcg ttggaagcac ggcagcagaa taaatatgag    660
aactacagca ccagcttctt catcagggac atcatcaaac cagacccgcc caagaacttg    720
cagatgaagc ctttgaagaa ctcacaggtg gaggtcagct gggagtaccc tgactcctgg    780
agcactcccc attcctactt ctccctcaag ttctttgttc gaatccagcg caagaaagaa    840
aagatgaagg agacagagga ggggtgtaac cagaaaggtg cgttcctcgt agagaagaca    900
tctaccgaag tccaatgcaa aggcgggaat gtctgcgtgc aagctcagga tcgctattac    960
aattcctcat gcagcaagtg ggcatgtgtt ccctgcagag tccgatcggt tcctggagta   1020
ggggtacctg gagtgggcag ggtcataccg gtctctggac ctgccaggtg tcttagccag   1080
tcccgaaacc tgctgaagac cacagatgac atggtgaaga cggccagaga aaagctgaaa   1140
cattattcct gcactgctga agacatcgat catgaagaca tcacacggga ccaaaccagc   1200
acattgaaga cctgtttacc actggaacta cacaagaacg agagttgcct ggctactaga   1260
gagacttctt ccacaacaag agggagctgc ctgccccac agaagacgtc tttgatgatg    1320
accctgtgcc ttggtagcat ctatgaggac ttgaagatgt accagacaga gttccaggcc   1380
atcaacgcag cacttcagaa tcacaaccat cagcagatca ttctagacaa gggcatgctg   1440
gtggccatcg atgagctgat gcagtctctg aatcataatg gcgagactct gcgccagaaa   1500
cctcctgtgg gagaagcaga cccttacaga gtgaaaatga agctctgcat cctgcttcac   1560
gccttcagca cccgcgtcgt gaccatcaac agggtgatgg gctatctgag ctccgcctaa   1620
```